(12) United States Patent
Gu

(10) Patent No.: US 11,234,961 B2
(45) Date of Patent: Feb. 1, 2022

(54) PAMOATE SALT OF MONOAMINE ANTI-PARKINSON'S AGENTS, METHOD OF PREPARATION AND USE THEREOF

(71) Applicant: Zi-Qiang Gu, Reston, VA (US)

(72) Inventor: Zi-Qiang Gu, Reston, VA (US)

( * ) Notice: Subject to any disclaimer, the term of this patent is extended or adjusted under 35 U.S.C. 154(b) by 144 days.

(21) Appl. No.: 16/639,170

(22) PCT Filed: Aug. 17, 2018

(86) PCT No.: PCT/US2018/046916
§ 371 (c)(1),
(2) Date: Feb. 14, 2020

(87) PCT Pub. No.: WO2019/036624
PCT Pub. Date: Feb. 21, 2019

(65) Prior Publication Data
US 2020/0230103 A1    Jul. 23, 2020

Related U.S. Application Data

(60) Provisional application No. 62/546,984, filed on Aug. 17, 2017.

(51) Int. Cl.
| A61K 31/381 | (2006.01) |
| A61K 9/00 | (2006.01) |
| A61K 31/404 | (2006.01) |
| A61K 31/428 | (2006.01) |

(52) U.S. Cl.
CPC .......... *A61K 31/381* (2013.01); *A61K 9/0019* (2013.01); *A61K 31/404* (2013.01); *A61K 31/428* (2013.01)

(58) Field of Classification Search
CPC .................................................. A61K 31/381
USPC ......................................................... 514/367
See application file for complete search history.

(56) References Cited

U.S. PATENT DOCUMENTS

| 2005/0181041 A1 | 8/2005 | Goldman |
| 2012/0022117 A1 | 1/2012 | Gruss et al. |
| 2014/0315952 A1 | 10/2014 | Gu |
| 2014/0377365 A1 | 12/2014 | Wu et al. |

FOREIGN PATENT DOCUMENTS

| WO | 2004/010999 A1 | 2/2004 |
| WO | 2005/014562 A1 | 2/2005 |
| WO | 2010/022140 A1 | 2/2010 |
| WO | 2014//205031 A1 | 12/2014 |

OTHER PUBLICATIONS

International Search Report for PCT/US2018/046916 dated Dec. 20, 2018, 3 pages.
Written Opinion of the ISA for PCT/US2018/046916 dated Dec. 20, 2018, 7 pages.

*Primary Examiner* — Nizal S Chandrakumar
(74) *Attorney, Agent, or Firm* — Nixon & Vanderhye P.C.

(57) ABSTRACT

In various embodiments, provided herein are pamoate salts of monoamine Anti-Parkinsons disease agents including rotigotine, ropinirole, pramipexole, selegiline, rasagiline, and safinamide, pharmaceutical composition comprising the same, methods of preparing the same, and methods of using the same. For example, the pamoate salt herein can be characterized by a molar ratio of rotigotine, ropinirole, pramipexole, selegiline, rasagiline, or safinamide to pamoic acid of about 1:1 or about 2:1. The pamoate salt herein can also be crystalline including anhydrous, hydrate or solvate forms, or their polymorphs, or amorphous. The pamoate salts described herein can provide a long acting and/or extended release profile of the monoamine agents for the treatment of Parkinsons disease (PD). Thus, also provided herein are methods of preparing a long acting and/or extended release injectable formulation of the monoamine agents using their respective pamoate salts. And in some embodiments, provided herein are methods of treating a subject in need thereof comprising administering a pharmaceutical composition comprising a pamoate salt of rotigotine, ropinirole, pramipexole, selegiline, rasagiline, and/or safinamide.

28 Claims, 26 Drawing Sheets

Figure 2.1

PAMOATE SALT OF MONOAMINE ANTI-PARKINSON'S AGENTS, METHOD OF PREPARATION AND USE THEREOF

CROSS REFERENCE TO RELATED APPLICATIONS

This application is the U.S. national phase of International Application No. PCT/US2018/046916 filed Aug. 17, 2018 which designated the U.S. and claims priority to U.S. Provisional Application No. 62/546,984, filed on Aug. 17, 2017, the entire contents of each of which are hereby incorporated by reference.

TECHNICAL FIELD

In various embodiments, the present invention generally relates to pamoate salts of anti-Parkinson's disease agents, for example, pamoate salts of rotigotine, ropinirole, pramipexole, selegiline, rasagiline, and/or safinamide, pharmaceutical compositions comprising such salts, methods of preparing such salts, and methods of treating a subject in need thereof with such salts and compositions.

BACKGROUND

Parkinson's disease (PD) is a motor system disorder of the nervous system. It is characterized as a progressive disorder that affects movement and results in the loss of dopamine-producing brain cells, causing tremor in the hands, arms, legs, jaw, and face and/or rigidity or stiffness of the limbs and trunk. The primary symptoms include muscular rigidity, slowness of movement, a resting tremor, and postural instability.

The most common anti-Parkinson's disease drugs are to either replace the dopamine levels in the brain, mimic the actions of dopamine or slow/inhibit the degradation of dopamine in the brain. The main categories of dopaminergic drugs include dopamine agonists such as rotigotine, ropinirole, and pramipexole, of which the chemical structures are depicted below. Drugs from the category of monoamine oxidase-B (MAO-B) inhibitors such as selegiline, rasagiline, and safinamide (see chemical structures below) increase the level of dopamine in the basal ganglia by blocking its metabolism. These drugs inhibit MAO-B which breaks down dopamine secreted by the dopaminergic neurons. The reduction in MAO-B activity results in increased L-DOPA in the nervous system thus alleviating the symptom from PD.

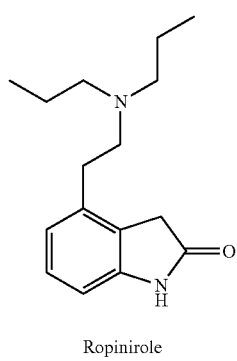

Ropinirole

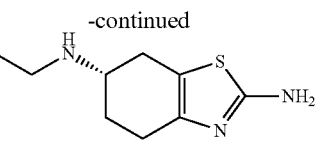

Pramipexole

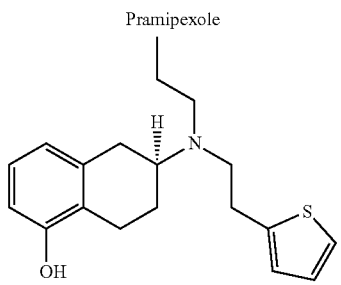

Rotigotine

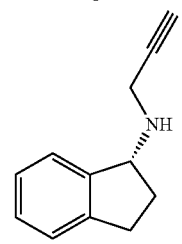

Selegiline

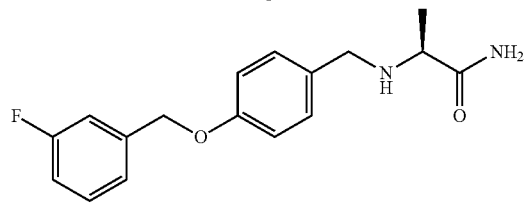

Rasagiline

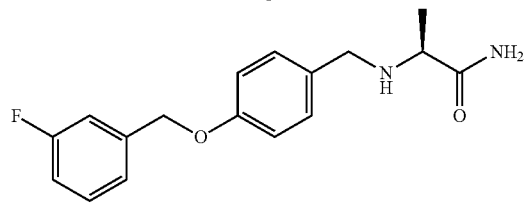

Safinamide

Currently available treatment of PD from the dopamine agonists and MAO-B inhibitors typically provide for daily oral administration. However, there is a need for a better dosing regimen of anti-PD drugs which can, for example, increase patient compliance and/or reduce side effects.

SUMMARY

In various embodiments, the present invention provides a variety of solid state forms, such as pamoate salts of anti-Parkinson's disease agents, e.g., monoamine anti-Parkinson's disease agents (hereinafter "monoamine agent(s)"), in different novel polymorphic forms, and more particularly, pamoate salts of rotigotine, pamoate salts of ropinirole, pamoate salts of pramipexole, pamoate salts of selegiline, pamoate salts of rasagiline, and/or pamoate salts of safinamide. In some embodiments, the present invention also provides pharmaceutical compositions comprising one or more of such salts, methods of preparing such salts, and methods of treating a subject or patient (such as a human) in need thereof with one or more of such salts and pharmaceutical compositions. In some embodiments, the present invention also provides formulations comprising one or more of the pamoate salts of the monoamine agents with a long acting and/or extended release profile. In any of the embodiments described herein, the monoamine agent can be rotigotine, ropinirole, pramipexole, selegiline, rasagiline, and/or safinamide. In any of the embodiments described herein, the monoamine agent can also be ropinirole, pramipexole, or rotigotine.

In some embodiments, the present invention provides novel pamoate salts, e.g., in different polymorphic forms, of monoamine agents. In some embodiments, the molar ratio of the monoamine agent's free base to pamoic acid is about 1:1 (which is referred to herein as the mono-pamoate salt of the monoamine agent). In some embodiments, the molar ratio of the monoamine agent's free base to pamoic acid is about 2:1 (which is herein referred as the semi-pamoate salt of the monoamine agent). In some embodiments, the pamoate salt of the monoamine agent is (1) crystalline, including anhydrous, hydrate, solvate forms and their polymorphs, or (2) amorphous. In some embodiments, the above salts can be especially useful in preparing a formulation, such as an extended release formulation (or composition) in which the release rate is minimally dependent on the pH of the environment at the injection site.

In some embodiments, the present invention provides a pharmaceutical composition comprising a pamoate salt of a monoamine agent and at least one pharmaceutically acceptable carrier. In some embodiments, the carrier is a viscous aqueous or nonaqueous carrier.

In some embodiments, the present invention provides a method of preparing a pamoate salt of a monoamine agent comprising treating or mixing the monoamine agent with pamoic acid or treating or mixing a salt of the monoamine agent with a pamoate salt in a solvent.

In some embodiments, the present invention provides a method of treating a subject having syndrome associated with Parkinson's disease comprising administering a therapeutically effective amount of a pamoate salt of a monoamine agent or a pharmaceutical composition comprising a pamoate salt of a monoamine agent and at least one pharmaceutically acceptable carrier to a subject in need of treatment thereof. In some embodiments, the composition is administered by injection. In some particular embodiments, the composition is administered intramuscularly or subcutaneously.

In some embodiments, the present invention provides a formulation (or composition) comprising a pamoate salt of a monoamine agent as an active ingredient or active agent, and one or more pharmaceutically acceptable carriers. In some embodiments, the formulation (or composition) can meet the unmet need for a stable, pharmaceutically suitable formulation with a controlled and/or sustained release rate which can be useful as a depot formulation or for intramuscular or subcutaneous use.

Additional embodiments and advantages of the disclosure will be set forth, in part, in the description that follows, and will flow from the description, or can be learned by practice of the disclosure. It is to be understood that both the foregoing summary and the following detailed description are exemplary and explanatory only, and are not restrictive of the invention as claimed.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention.

DETAILED DESCRIPTION OF THE INVENTION

Figure 1:
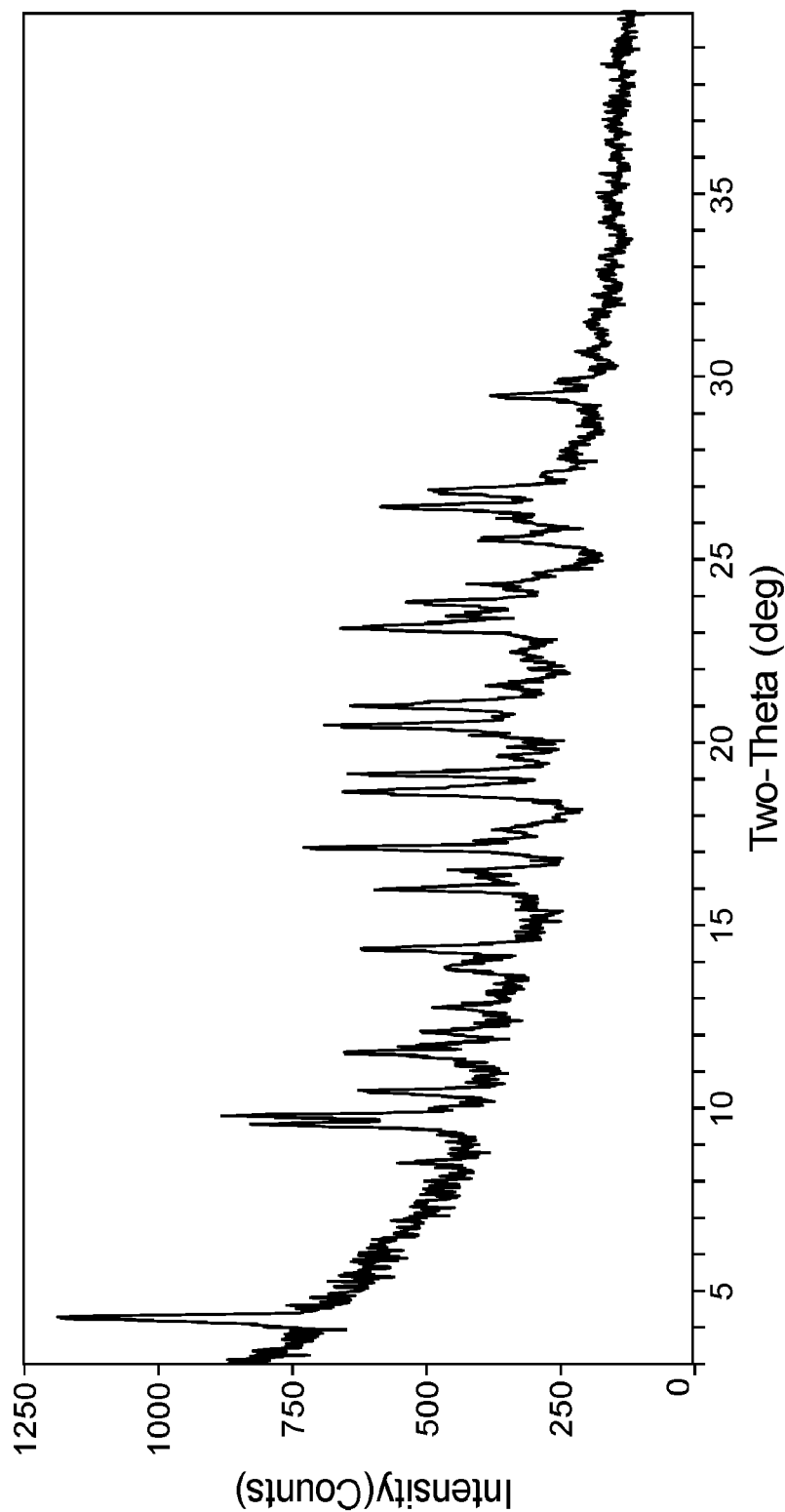
FIG. 1 depicts an X-ray powder diffraction ("XRPD") spectrum of ropinirole pamoate Form A (1:1 molar ratio of ropinirole to pamoic acid) obtained from a mixture of DMSO and water.

Prior to describing the details of the various embodiments of the invention, it is to be understood that the present invention is not limited in its application to the details of construction and the arrangement of components set forth in the following descriptions. The invention is capable of other embodiments and of being practiced or of being carried out in various ways by the ones skilled in the art.

It is also specifically understood that any numerical value recited herein includes all values from the lower value to the upper value, i.e., all possible combinations of numerical values between the lowest value and the highest value enumerated are to be considered to be expressly stated in the present application.

Currently available treatment of PD from the dopamine agonists and MAO-B inhibitors typically provide for daily oral administration. For example, pramipexole, a widely used dopamine agonist for the last decade as both monotherapy for patients with early Parkinson's disease as well as for patients with more advanced disease, is administered either three times a day or once daily. Unfortunately, development of motor and non-motor complications during the course of Parkinson's disease represents a major challenge for the current therapeutic management (M. Senek, D. Nyholm, *CNS Drugs.* 28(1):19-27, 2014). At advanced disease stages, patients frequently experience PD symptoms-such as bradykinesia- and dyskinesias, in response to fluctuations in drug concentrations. Studies indicated that continuous infusion of the dopamine agonist or intestinal infusion of levodopa reduce such fluctuations in both pharmacokinetics and motor function. These studies suggested that the continuous delivery of anti-PD drugs such as dopamine agonists would provide significant benefits alleviating the motor and non-motor complications. To these objectives, the effort has been made to develop continuous delivery formulation such as transdermal delivery of rotigotine and continuous subcutaneous infusion of apomorphine to provide more continuous drug concentrations, sustained benefits and minimized side effects. However, these regimens are far less optimal only providing daily short duration of continuous drug concentrations. Furthermore, long releasing regimen of more than 24 hours would also help patients with compliance as the patients with advanced PD are often non-compliant, making it difficult to assess whether or not a patient has received the proper dosage of medication. Taken together, there is still a significant benefit and unmet medical need to develop continuous drug delivery formulation of longer than 24 hours (e.g. extended release for 7 days) to better alleviate motor and non-motor complications for the PD patients.

Monoamine anti-PD agents are weak organic bases. In an alkaline solution (high pH), they exist as the free base form. Aqueous solubility of the monoamine agents increase with decreasing pH of the solution due to an increasing fraction of the drug being ionized. At high concentrations of the ionized drug (protonated amine), the salt form will precipitate out due to exceeding solubility product ($K_{sp}$). The nature of the drug and counter-ion determine the $K_{sp}$ and the associated solid state properties of the salt.

There are a wide range of counter-ions to prepare salts of bases using inorganic and organic acids. The most frequently used anions to form a salt of a basic drug is the hydrochloride form. For example, Requip XL, an extended-release tablet and a commercial product of dopamine agonist ropinirole for oral administration, is a hydrochloride salt. Transdermal patch of ropinirole also use its hydrochloride salt as active pharmaceutical ingredient (API) (U.S. Pat. No. 5,807,570 by Chen et al.). In the extended release tablet formulation, pramipexole dihydrochloride monohydrate was dispersed in a matrix comprising a hydrophilic polymer to achieve 24 hours release (U.S. Pat. No. 7,695,734 by Friedl et al. and U.S. Pat. No. 8,399,016 by Amidon et al.). Using benzene sulfonic acid salts of pramipexole has also been described in U.S. Pat. No. 7,365,086 by Eupen et al. as alternative pharmaceutical active agents. The administration of rotigotine hydrochloride in depot form has been described in the U.S. Pat. No. 8,604,076 by Rimpler et al. The depot regimen was intended to provide therapeutically significant plasma levels of rotigotine over a period of at least 24 hours after administration to a patient. These salts of the monoamine agents were prepared to improve physical properties including stability, solubility or increased dissolution rate for administration. The selection of the respective salts rendered them desirable properties for immediate or extended release dosage form. However, these formulations, even with extended release format, are administered for no longer than 24 hours. As a result, one objective is to provide improved methods of delivering the monoamine agents significantly less frequently than the current 24-hour dosing interval and formulations can be manufactured in a cost effective manner.

The present inventor has discovered that it is desirable to formulate the monoamine agents, e.g., in a depot formulation or as an injectable formulation such as an intramuscular or subcutaneous formulation, to assure consistent and proper dosage of the drug substance and to maximize the clinical benefits through maintaining a sustained and continuous drug concentration and improve patient compliance.

It is known that the pH of muscle tissue can fluctuate with exercise, stress, and injury which may impact drug solubility, and thus the rate of absorption of injectable drugs. Therefore, in some embodiments, it is also desirable to develop an injectable extended release formulation in which the release rate of the active ingredient is minimally dependent on pH fluctuation, such as those related to exercise, stress, and/or injury.

In some embodiments, the present inventor has found that a solid state or solid forms of anti-Parkinson's disease agents such as a monoamine anti-Parkinson's disease (anti-PD) agent pamoate salt, can be advantageous. Among other advantages, pamoate salts of the monoamine agents with specific polymorphic form and particle size distribution in a suitable formulation can provide a desired long acting and/or extended release profile. Such pamoate salts of the monoamine agent can provide an alternative and more desirable dosing regimen for treatment of patients suffering from Parkinson's disease (PD). It will also have superior drug absorption and distribution profiles compared to the existing oral drug products by providing a continuous delivery of drug, which would maintain stable plasma drug levels and reduce maximum to minimum plasma drug concentration ratio during dosing intervals, thus, ultimately improve safety profile and enhance clinical effectiveness.

The chemical structure of pamoic acid is:

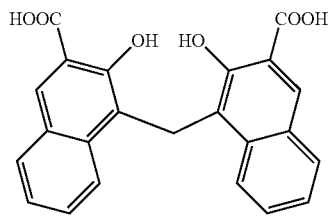 [SMILES: O=C(O)c1cc2ccccc2c(Cc2c(O)c(C(=O)O)cc3ccccc23)c1O]

The molecular weight of pamoic acid is 388 g/mol, the $pK_{a1}$ is 2.51, and $pK_{a2}$ is 3.1. With respect to the chemical structure of pamoic acid, both carboxylic counter ions can form salt with the amine of the monoamine agents, resulting in a molar ratio of the monoamine agents to pamoic acid of about 1:1 or about 2:1, such as those specified in FIGS. 1-20.

In one embodiment, the invention provides pamoate salts of anti-PD agents such as monoamine anti-PD agents and compositions and formulations containing said pamoate salts. Preferably, the pamoate salt is characterized by a molar ratio of the monoamine agent to pamoic acid of about 1:1 or about 2:1. The pamoate salt can be crystalline, anhydrous, hydrated, solvated, or amorphous.

In another embodiment, the invention provides pamoate salt of ropinirole, e.g., five crystalline Forms, Form A to Form E, of pamoate salt of ropinirole. Forms A, B, and D of pamoate salt of ropinirole each has a molar ratio of ropinirole to pamoic acid of about 1:1, whereas Forms C and E of pamoate salt of ropinirole each has a molar ratio of ropinirole to pamoic acid of about 2:1. Pamoate salts of ropinirole can be prepared by those skilled in the art in view of the present disclosure, see e.g., the Examples section. For example, Forms A, B, C, D, E of pamoate salt of ropinirole can be prepared by following the procedures described in Examples 1-5 in the Examples section, respectively.

In some embodiments, the crystalline Form A to Form E of pamoate salt of ropinirole can be characterized by one or more of the following properties: (1) an X-ray powder diffraction pattern having peak(s) expressed as 2-theta from 3 to 40 degrees substantially in accordance with (e.g., within ±0.2° 2-theta) one or more (e.g., two or more, three or more, etc., e.g., 1, 2, 3, 4, 5, 6, or more) of the main peaks shown in FIGS. 1, 3, 5, 7, 9, respectively, for each crystalline form; (2) an X-ray powder diffraction pattern substantially in accordance with those shown in FIGS. 1, 3, 5, 7, 9, respectively, for each crystalline form; (3) a differential scanning calorimetry thermogram pattern substantially in accordance with those shown in FIGS. 2, 4, 6, 8, 10, respectively, for each crystalline form; and (4) any combinations of (1), (2) and (3), respectively for each crystalline form. As used herein, "main peaks" refer to peaks in an XRPD spectrum (e.g., as shown in the FIGs and Tables herein) that have a relative intensity (height) of about 15% or more, preferably, about 30% or more (e.g., 35% or more, 50% or more, 60% or more, 70% or more, 80% or more, or 90% or more). In some embodiments, "main peaks" refers to peaks in an XRPD spectrum (e.g., as shown in the FIGs and Tables herein) that have a relative intensity (height) of about 80% or more.

For example, in some embodiments, ropinirole pamoate in crystalline Form A can be characterized by an XRPD spectrum having one or more (e.g., 4 or more, 6 or more, 8 or more, 10 or more, 12 or more, or all of) of the following peaks: 4.3, 9.8, 11.5, 14.4, 16.0, 17.1, 18.6, 19.1, 20.5, 21.0, 23.1, 23.8, 26.5, and 26.9, ±0.2° 2-theta. In some embodiments, ropinirole pamoate in crystalline Form A can be characterized by an XRPD spectrum having one or more (e.g., 2 or more, 4 or more, 6 or more, or all of) of the following peaks: 4.3, 9.8, 17.1, 18.6, 19.1, 20.5, 21.0, and 23.1, ±0.2° 2-theta. In some embodiments, ropinirole pamoate in crystalline Form A can be characterized by an XRPD spectrum having one or more (e.g., 1, 2, 3, or 4) of the following peaks: 4.3, 17.1, 18.6, and 20.5, ±0.2° 2-theta.

In some embodiments, ropinirole pamoate in crystalline Form B can be characterized by an XRPD spectrum having one or more (e.g., 4 or more, 6 or more, 8 or more, 10 or more, or all of) of the following peaks: 9.4, 11.5, 12.0, 12.7, 15.6, 16.4, 17.2, 18.7, 21.0, 23.1, 23.4, and 26.2, ±0.2° 2-theta. In some embodiments, ropinirole pamoate in crystalline Form B can be characterized by an XRPD spectrum having one or more (e.g., 2 or more, 4 or more, 6 or more, or all of) of the following peaks: 11.5, 12.0, 12.7, 16.4, 21.0, 23.1, 23.4, and 26.2, ±0.2° 2-theta. In some embodiments, ropinirole pamoate in crystalline Form B can be characterized by an XRPD spectrum having one or more (e.g., 2 or more, 4 or more, or all of) of the following peaks: 11.5, 16.4, 21.0, 23.1, 23.4, and 26.2, ±0.2° 2-theta.

In some embodiments, ropinirole pamoate in crystalline Form C can be characterized by an XRPD spectrum having one or more (e.g., 1, 2, 3, or 4) of the following peaks: 8.0, 9.5, 16.1, and 18.8, ±0.2° 2-theta. In some embodiments, ropinirole pamoate in crystalline Form C can be characterized by an XRPD spectrum having peaks at 16.1 and 18.8, ±0.2° 2-theta.

In some embodiments, ropinirole pamoate in crystalline Form D can be characterized by an XRPD spectrum having one or more (e.g., 1, 2, 3, 4, 5, or 6) of the following peaks: 14.3, 17.9, 21.5, 22.4, 24.8, and 25.2, ±0.2° 2-theta. In some embodiments, ropinirole pamoate in crystalline Form D can be characterized by an XRPD spectrum having one or more (1, 2, or 3) of the following peaks: 14.3, 17.9, and 25.2, ±0.2° 2-theta, for example, ropinirole pamoate in crystalline Form D can be characterized by an XRPD spectrum having a peak at 17.9±0.2° 2-theta.

In some embodiments, ropinirole pamoate in crystalline Form E can be characterized by an XRPD spectrum having one or more (e.g., 4 or more, 6 or more, 8 or more, 10 or more, or all of) of the following peaks: 11.1, 11.7, 12.0, 15.5, 18.8, 19.6, 20.2, 21.0, 22.9, 23.6, 26.1, and 26.6, ±0.2° 2-theta. In some embodiments, ropinirole pamoate in crystalline Form E can be characterized by an XRPD spectrum having one or more (e.g., 2 or more, 4 or more, or all of) of the following peaks: 11.1, 11.7, 12.0, 21.0, 26.1, and 26.6, ±0.2° 2-theta. In some embodiments, ropinirole pamoate in crystalline Form E can be characterized by an XRPD spectrum having one or more (e.g., 1, 2, or 3) of the following peaks: 11.7, 12.0, and 21.0, ±0.2° 2-theta.

In some embodiments, each of the crystalline Form A to Form E of pamoate salts of ropinirole can be substantially pure, for example, each form can be substantially free of other crystalline or amorphous forms of pamoate salts of ropinirole (e.g., less than 20%, less than 10%, less than 5%, or not detectable with the XRPD method described herein). However, in some embodiments, each of the crystalline Form A to Form E of pamoate salts of ropinirole can exist in a mixture with one or more other forms of pamoate salts of ropinirole, crystalline or amorphous.

In yet another embodiment, the invention relates to pamoate salt of rotigotine, e.g., crystalline Form I of pamoate salt of rotigotine, which has a molar ratio of rotigotine to pamoic acid of about 1:1. Pamoate salts of rotigotine can be prepared by those skilled in the art in view of the present disclosure, see e.g., the Examples section. For example, Form I of pamoate salt of rotigotine can be prepared by following the procedures described in Example 6 in the Examples section.

In some embodiments, the crystalline Form I of pamoate salt of rotigotine can be characterized by one or more of the following properties: (1) an X-ray powder diffraction pattern having peak(s) expressed as 2-theta from 3 to 40 degrees substantially in accordance (e.g., within ±0.2° 2-theta) one or more (e.g., two or more, three or more, etc., e.g., 1, 2, 3, 4, 5, 6, or more) of with the main peaks shown in FIG. 11; (2) an X-ray powder diffraction pattern substantially in accordance with that shown in FIG. 11; (3) a differential scanning calorimetry thermogram pattern substantially in accordance with that shown in FIG. 12; and (4) any combinations of (1), (2) and (3). For example, in some embodiments, Form I of pamoate salt of rotigotine can be characterized by an XRPD spectrum having one or more (e.g., 1, 2, 3, 4, 5, 6, 7, or 8) of the following peaks: 4.6, 9.3, 17.5, 18.7, 24.2, 26.4, 28.2, and 29.6, ±0.2° 2-theta. In some embodiments, Form I of pamoate salt of rotigotine can be characterized by an XRPD spectrum having one or both peaks at 4.6 and 9.3, ±0.2° 2-theta. In some embodiments, the crystalline Form I of pamoate salt of rotigotine can be substantially pure, for example, substantially free of other crystalline or amorphous forms of pamoate salt of rotigotine (e.g., less than 20%, less than 10%, less than 5%, or not detectable with the XRPD method described herein). However, in some embodiments, the crystalline Form I of pamoate salt of rotigotine can exist in a mixture with one or more other forms of pamoate salt of rotigotine, crystalline or amorphous.

In yet another embodiment, the invention relates to pamoate salt of pramipexole, e.g., crystalline forms, Form 1 to Form 4, of pamoate salt of pramipexole. Pamoate salts of pramipexole can be prepared by those skilled in the art in view of the present disclosure, see e.g., the Examples section. For example, Forms 1-4 of pamoate salt of pramipexole can be prepared by following the procedures described in Examples 7-10 in the Examples section, respectively.

Forms 1 and 2 of pamoate salt of pramipexole each has a molar ratio of pramipexole to pamoic acid of about 1:1, whereas Forms 3 and 4 of pamoate salt of pramipexole each has a molar ratio of pramipexole to pamoic acid of about 2:1. In some embodiments, the crystalline Form 1 to Form 4 of pamoate salt of pramipexole can be characterized by one or more of the following properties: (1) an X-ray powder diffraction pattern having peak(s) expressed as 2-theta from 3 to 40 degrees substantially in accordance with (e.g., within ±0.2° 2-theta) one or more (e.g., two or more, three or more, etc., e.g., 1, 2, 3, 4, 5, 6, or more) of the main peaks shown in FIG. 13, 15, 17, 19, respectively, for each crystalline form; (2) an X-ray powder diffraction pattern substantially in accordance with those shown in FIG. 13, 15, 17, 19, respectively, for each crystalline form; (3) a differential scanning calorimetry thermogram pattern substantially in accordance with those shown in FIG. 14, 16, 18, 20, respectively for each crystalline form; and (4) any combinations of (1), (2) and (3).

In some embodiments, Form 1 of pamoate salt of pramipexole can be characterized by an XRPD spectrum having one or more (e.g., 1, 2, 3, 4, 5, 6, 7, 8, or 9) of the following peaks: 7.7, 11.8, 13.8, 15.3, 18.9, 21.1, 23.1, 23.7, and 26.4, ±0.2° 2-theta. In some embodiments, Form 1 of pamoate salt of pramipexole can be characterized by an XRPD spectrum having one or more (e.g., 1, 2, or 3) of the following peaks: 13.8, 15.3, and 21.1, ±0.2° 2-theta.

In some embodiments, Form 2 of pamoate salt of pramipexole can be characterized by an XRPD spectrum having one or more (e.g., 1, 2, 3, 4, 5, 6, 7, or 8) of the following peaks: 12.0, 15.0, 17.2, 20.4, 20.9, 22.5, 23.3, and 25.4, ±0.2° 2-theta. In some embodiments, Form 2 of pamoate salt of pramipexole can be characterized by an XRPD spectrum having one or more (e.g., 1, 2, 3, 4, 5, or 6) of the following peaks: 12.0, 15.0, 20.4, 20.9, 22.5, and 23.3, ±0.2° 2-theta. In some embodiments, Form 2 of pamoate salt of pramipexole can be characterized by an XRPD spectrum having one or more (e.g., 1, 2, 3, or 4) of the following peaks: 12.0, 15.0, 20.4, and 20.9, ±0.2° 2-theta.

In some embodiments, Form 3 of pamoate salt of pramipexole can be characterized by an XRPD spectrum having one or more (e.g., 1, 2, 3, 4, 5, 6, 7, or 8) of the following peaks: 10.7, 12.7, 13.5, 14.9, 16.3, 18.1, 18.7, and 22.3, ±0.2° 2-theta. In some embodiments, Form 3 of pamoate salt of pramipexole can be characterized by an XRPD spectrum having one or more (e.g., 1, 2, 3, 4, 5, or 6) of the following peaks: 10.7, 12.7, 13.5, 14.9, 18.7, and 22.3, ±0.2° 2-theta. In some embodiments, Form 3 of pamoate salt of pramipexole can be characterized by an XRPD spectrum having one or more (e.g., 1, 2, 3, or 4) of the following peaks: 10.7, 12.7, 13.5, and 14.9, ±0.2° 2-theta.

In some embodiments, Form 4 of pamoate salt of pramipexole can be characterized by an XRPD spectrum having one or more (e.g., 1, 2, 3, 4, 5, 6, 7, 8, 9, or 10) of the following peaks: 6.1, 13.5, 14.9, 17.9, 18.9, 21.3, 21.8, 22.4, 23.2, and 24.0, ±0.2° 2-theta. In some embodiments, Form 4 of pamoate salt of pramipexole can be characterized by an XRPD spectrum having one or more (e.g., 1, 2, 3, 4, 5, or 6) of the following peaks: 6.1, 17.9, 18.9, 21.3, 23.2, and 24.0, ±0.2° 2-theta. In some embodiments, Form 4 of pamoate salt of pramipexole can be characterized by an XRPD spectrum having one or more (e.g., 1, 2, 3, or 4) of the following peaks: 6.1, 17.9, 21.3, and 23.2, ±0.2° 2-theta. In some embodiments, Form 4 of pamoate salt of pramipexole can be characterized by an XRPD spectrum having the following peaks: 6.1 and 17.9, ±0.2° 2-theta.

In some embodiments, each of the crystalline Form 1 to Form 4 of pamoate salt of pramipexole can be substantially pure, for example, each form can be substantially free of other crystalline or amorphous forms of pamoate salt of pramipexole (e.g., less than 20%, less than 10%, less than 5%, or not detectable with the XRPD method described herein). However, in some embodiments, each of the crystalline Form 1 to Form 4 of pamoate salt of pramipexole can exist in a mixture with one or more other forms of pamoate salt of pramipexole, crystalline or amorphous.

In some embodiments, the invention further provides a pharmaceutical composition comprising one or more of the pamoate salts of the monoamine anti-PD agents (e.g., any of those described herein, e.g., Forms A-E of pamoate salt of ropinirole, Form I of pamoate salt of rotigotine, Forms 1-4 of pamoate salt of pramipexole) and at least one pharmaceutically acceptable carrier. In some embodiments, the pharmaceutical composition is an intramuscularly or subcutaneously injectable formulation. In one preferred embodiment, the pharmaceutical composition is an extended release formulation comprising pamoate salts of the monoamine agents and a polymer (e.g., a release control polymer). Polymers suitable for use in the extended release formulations include any of those known in the art. Some of which can be found, for example, in Remington's Pharmaceutical Sciences, latest edition, Mack Publishing Co. In some embodiments, the extended release can be based on the slow dissolution rate of the pamoate salts herein. In some embodiments, the extended release formulation can also be free or substantially free of a polymer, for example, the extended release formulation can be free or substantially free a release control polymer.

In another embodiment, the pharmaceutically acceptable carrier is a viscous aqueous or nonaqueous fluid. In some embodiments, the viscous aqueous or nonaqueous fluid can have a viscosity of at least 20 cp at 20° C. In some embodiments the viscous aqueous or nonaqueous fluid can have a viscosity at 20° C. of at least about 30 cp, e.g., about 40 cp, about 50 cp, about 60 cp, at least about 40 cp, at least about 50 cp, or at least about 60 cp. In a preferred embodiment, the pharmaceutical composition releases an effective amount of the active agent (one or more of the pamoate salts of the monoamine agents as described herein) over a period of at least about 24 hours or at least about 48 hours. In another preferred embodiment, the active agent in the pharmaceutical composition has a duration of efficacy of at least about 7 days or at least about 14 days.

The invention further relates to methods of treating a subject having syndrome associated with Parkinson's disease, such as a warm blood mammal (such as a human patient or subject characterized as having Parkinson's disease). The method comprises administering a therapeutically effective amount of a pharmaceutical composition comprising a pamoate salt of the monoamine agent (e.g., any of those described herein) and at least one pharmaceutically acceptable carrier.

In various embodiments, the present inventor discovered that the pharmaceutically acceptable salts of the monoamine agents formed using pamoic acid as a counterion surprisingly exhibit very low solubility ($K_{sp}$). This low solubility can be highly desirable when used in a pharmaceutical composition to provide for extended release of the pamoate salt of the monoamine agents, for example, when administered intramuscularly or subcutaneously. In some embodiments, the pharmaceutical compositions of the present invention include various pharmaceutical dosage forms for the purposes of administering dosage to a subject (such as a warm blooded mammal, such as a human) in need of treatment of Parkinson's disease. In some embodiments, to prepare the pharmaceutical compositions of the present invention, a pharmaceutically effective amount of one or more pamoate salts of the monoamine agent (as the active ingredient or active agent) are combined with one or more pharmaceutically acceptable excipients. The pharmaceutically acceptable excipients used are generally less critical, are well known in the art, and may take a wide variety of forms depending on the form of preparation desired for administration. In some embodiments, these pharmaceutical compositions are provided in a unit dosage form suitable for administration.

Administration of the compositions of the present invention can be, for example, parenterally, such as by subcutaneous or intramuscular injection or implantation. For administration, the pamoate salts of the monoamine agents can be, for example, suspended in an aqueous solvent, which can further comprise a wetting agent, such as the polyoxyethylene derivatives of sorbitan esters, e.g. polysorbate 80 (Tween® 80) and polysorbate 20 (Tween® 20), lecithin, polyoxyethylene- and polyoxypropylene ethers, sodium deoxycholate, and the like; a suspending agent such as a cellulose derivate, e.g. methylcellulose, sodium carboxymethylcellulose and hydroxypropyl methylcellulose, polyvinylpyrrolidone, alginates, chitosan, dextran, gelatin, polyethylene glycols, polyoxyethylene- and polyoxypropylene ethers and the like; an acid, e.g. hydrochloric acid, and the like; a base, e.g. sodium hydroxide, and the like; a buffer comprising a mixture of appropriate amounts of an acid such as phosphoric, succinic, tartaric, lactic, acetic, maleic or citric acid, and a base, in particular sodium hydroxide or disodium hydrogen phosphate; a preservative, e.g. benzoic acid, benzyl alcohol, butylated hydroxyanisole, butylated hydroxytoluene, chlorbutol, a gallate, a hydroxybenzoate, EDTA, phenol, chlorocresol, metacresol, benzothonium chloride, myristyl-.gamma-piccolinium chloride, phenylmercuri acetate, thimerosal and the like; a tonicity adjusting agent, e.g. sodium chloride, dextrose, mannitol, sorbitol, lactose, sodium sulfate, and the like. In some embodiments, the pamoate salts of the monoamine agents can also be formulated in one or more oils. Appropriate oils that can be used include fixed oils, for example, peanut oil, sesame oil, cottonseed oil, corn oil, safflower oil, castor oil, ethyloleate, soybean oil, synthetic glycerol esters of long chain fatty or medium chain acids and mixtures of these and other oils. In some embodiments, thickening agents can be added to the composition, e.g. aluminum monostearate, ethylcellulose, triglycerides, hydrogenated castor oil, and the like.

In view of the usefulness of the pamoate salts of the monoamine agents in the treatment of Parkinson's diseases, in some embodiments, the present invention further provides a method of treating warm-blooded mammals (such as humans), suffering from PD. In some embodiments, the method comprises administering a therapeutically effective amount of a pharmaceutical composition comprising at least one pamoate salt of the monoamine agents as described herein and one or more pharmaceutically acceptable excipients.

In some embodiments, the pharmaceutical compositions described herein can be administered to a subject in need of treatment of Parkinson's disease as a long acting composition. In one embodiment, the active agent is released from the composition over a period of at least about 24 hours, preferably at least about 48 hours. The active agent can also be administered in an extended release composition. In one embodiment, the extended release composition releases the active agent over a period of at least about 7 days, preferably at least about 14 days, alternatively for at least 2 weeks, at least 3 weeks, at least 4 weeks, at least 6 weeks or at least 8 weeks. The composition can be administered by injection, such as intramuscularly or subcutaneously. In one embodiment, the compositions can be administered as a single or sole dose. However, in some embodiments, the compositions described herein are particularly beneficial for those subjects in need of treatment of Parkinson's disease that require constant or chronic therapy, such as those subjects that receive repeated doses over several weeks or months or more. In such dosing regimens, the method can comprise: (1) administering as first dose an first extended release composition containing one or more of the pamoate salts of the monoamine agents as described herein followed by (2) administering as a second dose (and as subsequence doses if necessary), a second extended release composition. The second extended release composition can be the same, substantially the same or different than the first extended release composition. Specifically, in some embodiments, the second extended release composition can include as the active agent of one or more of the pamoate salts of the monoamine agents as described herein or an active agent that is other than the pamoate salts of the monoamine agents as described herein. The second composition can be administered at about 7 days, or more, such as at least about 14 days, or at least about 21 days, after the first administration of the first extended release composition, where the first administration results in the release of active agent for a period of 1 day, 2 days, 3 days, 4 days, 5 days, 6 days, 7 days, 8 days, 9 days, 10 days, 11 days, 12 days, 13 days, 14 days, or more.

As used herein, the term "about" modifying an amount related to the invention refers to variation in the numerical quantity that can occur, for example, through routine testing and handling; through inadvertent error in such testing and handling; through differences in the manufacture, source, or purity of ingredients employed in the invention; and the like. As used herein, "about" a specific value also includes the specific value, for example, about 10% includes 10%. Whether or not modified by the term "about", the claims include equivalents of the recited quantities. In one embodiment, the term "about" means within 20% of the reported numerical value.

As used herein, the term "individual", "subject" or "patient" refers to a warm blooded animal which is afflicted with a particular disease state. Warm blooded animals include mammals, such as humans.

The term "effective amount" or "therapeutically effective amount" is defined as an amount resulting in the improvement of any parameters or clinical symptoms. In any of the embodiments described in, the term "effective amount" or "therapeutically effective amount" can be an amount resulting in the improvement of any parameters or clinical symptoms associated with Parkinson's disease. The actual dose may vary with each patient and does not necessarily indicate a total elimination of all disease symptoms. A therapeutically effective amount of the compound used in the methods described herein can be readily determined by one skilled in the art, such as an attending physician, by observing results obtained under analogous circumstances and by using conventional techniques. In determining the therapeutically effective dose, the attending physician considers a number of factors, including, but not limited to: the species of mammal; its size, age, and general health; the specific disease involved; the degree of involvement or the severity of the disease; the response of the individual patient; the particular compound administered; the mode of administration; the bioavailability characteristic of the preparation administered; the dose regimen selected; the use of concomitant medication; and other relevant circumstances.

Similarly, the term "duration of efficacy" or "therapeutically effective plasma concentration" of a monoamine for a given time period should be understood as such that during such time period, the respective monoamine is present (e.g., in the plasma of a subject treated with the pamoate salt herein) in an amount and/or concentration sufficient to result in the improvement of any parameters or clinical symptoms, for example, the improvement of any parameters or clinical symptoms associated with Parkinson's disease.

Preferred amounts and modes of administration can be readily be determined by one skilled in the art depending upon the particular characteristics of the compound selected, the disease state to be treated, the stage of the disease, and other relevant circumstances using formulation technology known in the art, described for example in Remington's Pharmaceutical Sciences, latest edition, Mack Publishing Co.

Pharmaceutical compositions can be manufactured utilizing routine techniques known in the art. Typically a therapeutically effective amount of the compound (salt) will be combined with a pharmaceutically acceptable carrier.

The pharmaceutical compositions of the present invention can be administered parenterally. For instance, they can be administered by injection. Preferred methods of parenteral administration include intramuscular and subcutaneous injection.

For parenteral administration, the compounds (salt) can be dissolved in a physiologically acceptable pharmaceutical carrier and administered as either a solution or a suspension. Viscous injectable carriers are preferred, having for example, a viscosity of at least 20 cp at 20° C. In other embodiments, the fluid phase of the suspension has a viscosity at 20° C. of at least about 30 cp, e.g., about 40 cp, about 50 cp, about 60 cp, at least about 40 cp, at least about 50 cp, or at least about 60 cp. The composition can also comprise a viscosity enhancing agent, a density enhancing agent, a tonicity enhancing agent, and/or a wetting agent. Suitable pharmaceutical carriers include water, saline, dextrose solutions, fructose solutions, ethanol, or oils of animal, vegetative, or synthetic origin. The pharmaceutical carrier may also contain preservatives, and buffers as known in the art.

When the composition is to be used as an injectable material, including, but not limited to, needle-less injection, it can be formulated into a conventional injectable carrier. Suitable carriers include biocompatible and pharmaceutically acceptable solutions, emulsions or suspensions.

In another embodiment, the formulation can be surgically implanted. Such formulations can include any of the well-known biodegradable and bioerodible carriers, such as polylactides, poly-lactide-co-glycolides and collagen formulations. Such materials can be in the form of solid implants, sponges, and the like. In any event, for local use of the materials, the active ingredients usually are present in the carrier or excipient in a weight ratio of from about 1:1000 to 1:20,000, but are not limited to ratios within this range.

In some embodiments, the present invention also provides methods of making pamoate salts of the monoamine agents. Specifically, pamoate salts of the monoamine agents can be prepared in a variety of different ways. For example, in one embodiment, pamoate salts of the monoamine agents can be prepared directly by treating or mixing the monoamine agents (such as a free base) with pamoic acid in a solvent (such as water, ethanol or DMSO). In another embodiment, pamoate salts of the monoamine agents can be prepared by treating or mixing the monoamine agents salt (such as a hydrochloride salt) with a pamoate salt (such as disodium pamoate) in one or more solvents. For example, the pamoate of the monoamine agents can be prepared by adding a solution of disodium pamoate, or other pamoate salt in an appropriate solvent, such as water, to a solution of the monoamine agent hydrochloride and leaving the solution to stir for a period of time, such as, for example, about 3 or 12 hours, until precipitation occurs. Alternatively, other methods such as evaporation, slurry, anti-solvent, cooling and hydration can also be used to crystalize the salt. Solvents useful for preparing the pamoate salts herein include, without limitation, water, alkanols (e.g. methanol and ethanol), alkyl ketones (e.g. acetone), alkanes (e.g. n-heptane), acetonitrile, toluene, DMSO, alkyl ester (e.g. ethyl acetate), halogenated alkanes (e.g. chloroform), ethers, tetrahydrofuran (THF), 1,4-dioxane, and combinations thereof.

In some embodiments, the present invention provides a solid state form of pharmaceutical acceptable salt of dopamine agonists rotigotine, ropinirole, and pramipexole, wherein the salt is a pamoate salt. The pamoate salt can be crystalline, anhydrous, hydrated, solvated, or amorphous. In another embodiment, the invention relates to crystalline pamoate salts of rotigotine, ropinirole, or pramipexole having or characterized by one or more of the following properties: (1) an X-ray powder diffraction pattern substantially in accordance with those shown in FIGS. 1, 3, 5, 7, 9, 11, 13, 15, 17, 19, respectively, for each crystalline form; (2) a differential scanning calorimetry thermogram pattern substantially in accordance with those shown in FIGS. 2, 4, 6, 8, 10, 12, 14, 16, 18, 20, respectively, for each crystalline form; and (3) a combination of (1) and (2). In some embodiments, the present invention also relates to compositions containing one or more of the above described pamoate salts of rotigotine, ropinirole, and pramipexole and pharmaceutical compositions containing said compositions and at least one pharmaceutically acceptable carrier.

In some embodiments, the present invention provides a solid state form of a pharmaceutical acceptable salt of anti-PD MAO-B inhibitors selegiline, rasagiline, and safinamide, wherein the salt is a pamoate salt. The pamoate salt can be crystalline, anhydrous, hydrated, solvated, or amorphous. In some embodiments, the present invention also provides compositions containing one or more of the above described pamoate salts of selegiline, rasagiline, and safinamide and pharmaceutical compositions containing said compositions and at least one pharmaceutically acceptable carrier.

The following examples are intended to illustrate and not to limit the scope of the present invention.

EXAMPLES

Example 1

Preparation of Ropinirole Pamoate at a 1:1 Molar Ratio of Ropinirole to Pamoic Acid from a Mixture of DMSO and Water.

Ropinirole (2 g, 7.7 mmol) and Pamoic Acid (2.975 g, 7.7 mmol) was added into DMSO (15 mL) with stirring to form a solution. The resultant solution was slowly added to water (500 mL) at room temperature which produced a white solid. The solid was collected on a filter, washed with water, and dried in vacuum at 40° C. to generate Ropinirole Pamoate as white solids (4.0 g, 80.4%).

X-ray powder diffraction ("XRPD") patterns of above solids were obtained using a Bruker D8 Advance x-ray powder diffractometer with copper Kα radiation at a wavelength of 1.54 nm. Instrumental conditions included a step size of 0.02 degree per step, a scan rate of 0.2 seconds per step, a 2-theta range of 3 to 40 degrees, a voltage of 40 kV, a current of 40 mA, and a Lynxeye detector. Samples were packed into recessed sample holders for analysis. Typically, the error margin for 2-theta values is ±0.2°. XRPD patterns for other examples herein were obtained similarly. A typical example of X-ray powder diffraction pattern and data, respectively, for the salt from Example 1 is shown in FIG. 1 and Table 1 wherein d(A) represents the interplanar spacing. Height and Height % represent the typical relative intensities.

Figure 2:
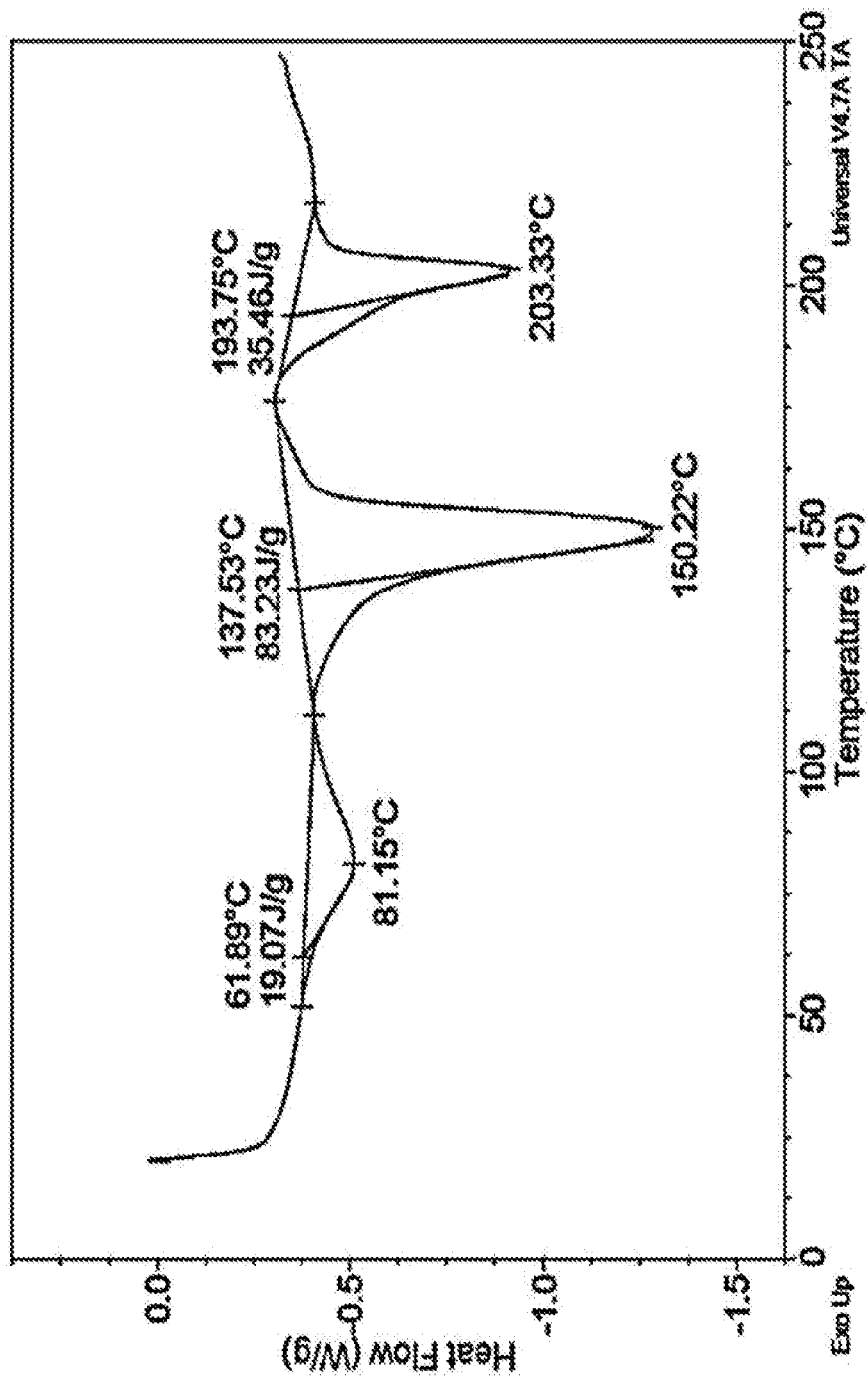
FIG. 2 depicts a differential scanning calorimetry ("DSC") thermogram of ropinirole pamoate Form A (1:1 molar ratio of ropinirole to pamoic acid) obtained from a mixture DMSO and water.
Figure 23:
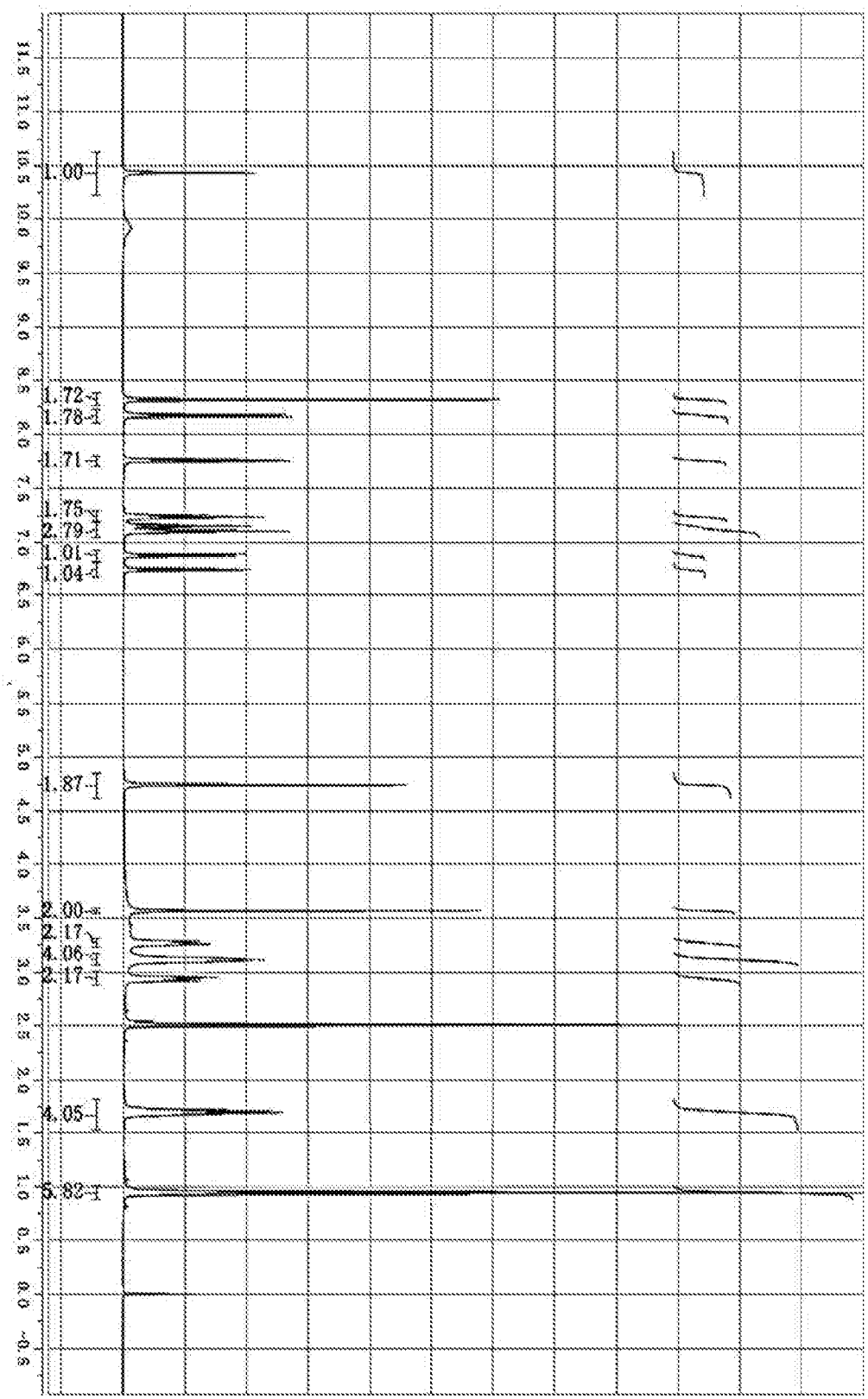
FIG. 23 depicts a $^1$H-NMR spectrum of Ropinirole pamoate (1:1 molar ratio of Ropinirole to pamoic acid) obtained from Example 1.

The differential scanning calorimetry thermogram of above solids was obtained using a TA Instrument Q200 Differential Scanning calorimeter. The measurement was controlled by "Thermal Advantage" system and data was analyzed using "Universal Analysis" software. Typical sample load ranges from 0.5 to 5 mg. The measurement is under an atmosphere of nitrogen with flow rate of 40 mL/min. System equilibrium is set at 20° C. and the temperature is then increased to 250° C. at a rate of 10° C./min Typically, the error margin for DSC peak values is ±3° C. DSC thermograms for other examples herein were obtained similarly. A typical example of a differential scanning calorimetry thermogram for the salt from Example 1 is shown in FIG. 2. $^1$H NMR (see FIG. 23) indicates that the molar ratio of Ropinirole to Pamoic Acid in the salt from Example 1 is about 1:1.

TABLE 1

| 2-Theta | d(A) | Height | Height % |
|---|---|---|---|
| 4.279 | 20.6311 | 469 | 100.0 |
| 8.508 | 10.3844 | 131 | 26.8 |
| 9.760 | 9.0644 | 370 | 75.7 |
| 10.479 | 8.4352 | 236 | 48.3 |
| 11.523 | 7.6727 | 286 | 68.9 |
| 12.096 | 7.3111 | 134 | 27.4 |
| 12.746 | 6.9366 | 140 | 28.6 |
| 13.845 | 6.3908 | 146 | 29.7 |
| 14.363 | 6.1616 | 316 | 64.6 |
| 15.971 | 6.5446 | 319 | 65.2 |
| 16.504 | 6.3669 | 173 | 35.4 |
| 17.126 | 6.1732 | 461 | 94.3 |
| 17.608 | 6.0326 | 121 | 24.7 |
| 18.646 | 4.7543 | 400 | 81.8 |
| 19.146 | 4.6317 | 382 | 78.1 |
| 19.615 | 4.5222 | 78 | 16.0 |
| 20.467 | 4.3357 | 396 | 81.0 |
| 21.007 | 4.2258 | 369 | 75.5 |
| 21.653 | 4.1196 | 103 | 21.1 |
| 22.471 | 3.9533 | 62 | 12.7 |
| 23.111 | 3.8452 | 369 | 75.5 |
| 23.831 | 3.7307 | 274 | 56.0 |
| 24.328 | 3.6556 | 142 | 29.0 |
| 25.517 | 3.4879 | 173 | 35.4 |
| 26.052 | 3.4174 | 90 | 18.4 |
| 26.450 | 3.3670 | 342 | 69.9 |
| 26.910 | 3.3105 | 259 | 53.0 |
| 29.473 | 3.0281 | 207 | 42.3 |
| 29.914 | 2.9644 | 75 | 15.3 |
| 30.686 | 2.9112 | 65 | 11.2 |
| 31.494 | 2.8362 | 45 | 9.2 |
| 34.236 | 2.6170 | 42 | 8.6 |
| 38.553 | 2.3333 | 44 | 9.0 |

Example 2

Figure 3:
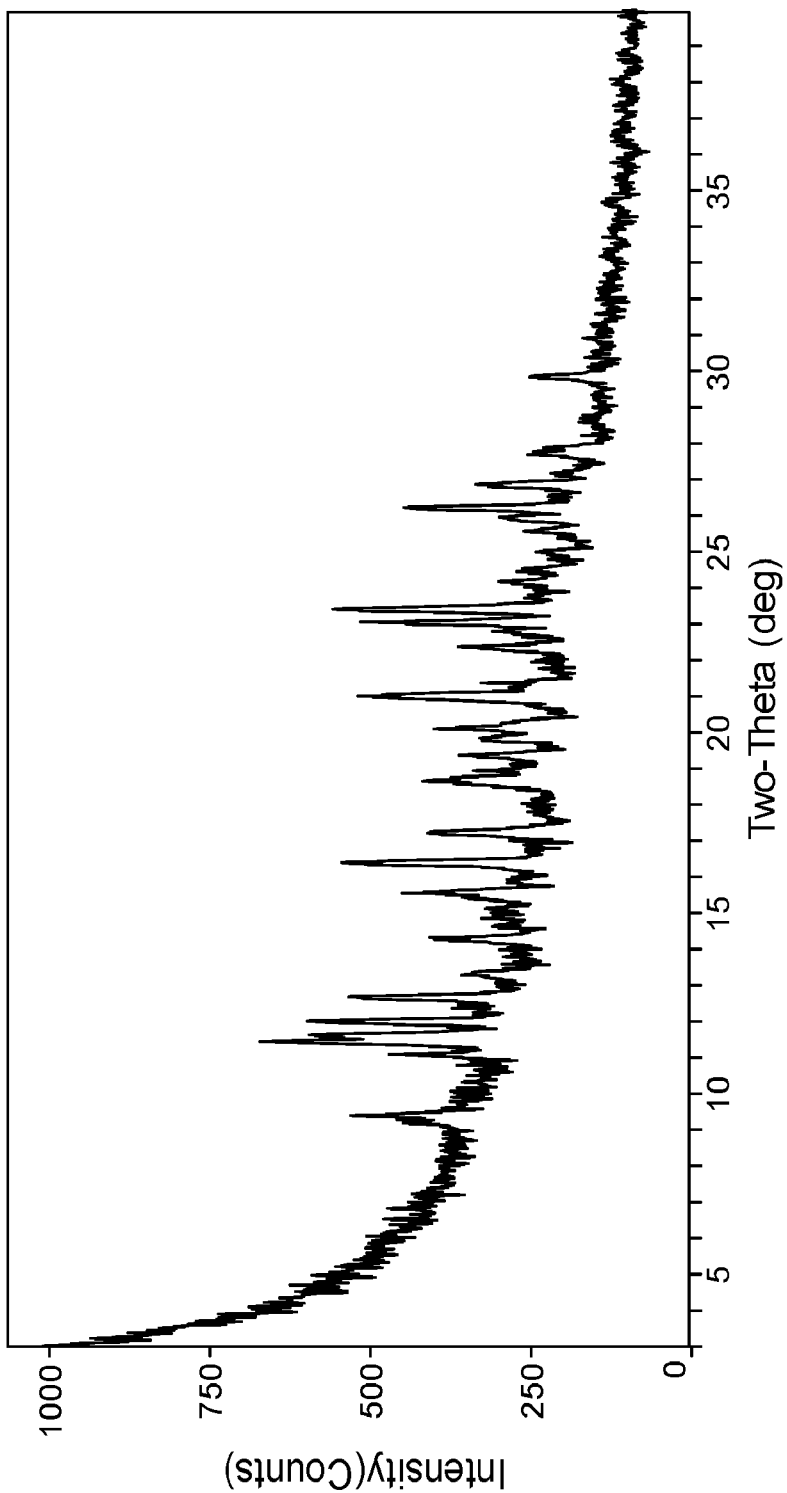
FIG. 3 depicts an XRPD spectrum of ropinirole pamoate Form B (1:1 molar ratio of ropinirole to pamoic acid) obtained from heating materials depicted in FIGS. 1 and 2 at 170° C. for 30 minutes.
Figure 4:
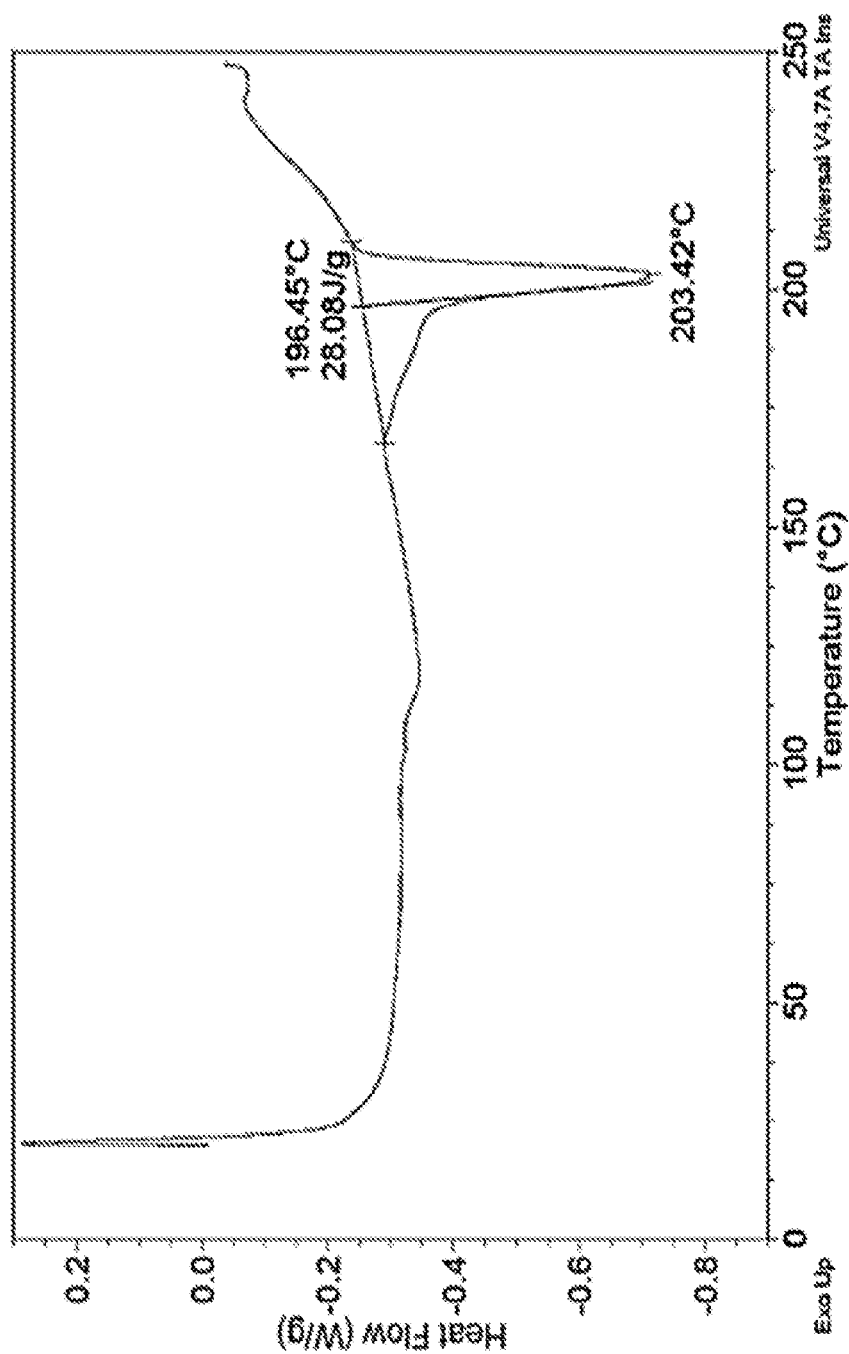
FIG. 4 depicts a DSC thermogram of ropinirole pamoate Form B (1:1 molar ratio of ropinirole to pamoic acid) obtained from heating materials depicted in FIGS. 1 and 2 at 170° C. for 30 minutes.

Preparation of Ropinirole Pamoate at a 1:1 Molar Ratio of Ropinirole to Pamoic Acid from Heating Batches Depicted in FIGS. 1 and 2 at 170° C. for 30 Minutes 75 mg of ropinirole pamoate from Example 1 was placed at 170° C. for 30 minutes to give a solid of which a typical example of an X-ray diffraction pattern is shown in FIG. 3 and Table 2. A typical example of a differential scanning calorimetry thermogram for this solid is shown in FIG. 4. $^1$H NMR indicates that the molar ratio of Ropinirole to Pamoic Acid in this solid is about 1:1.

TABLE 2

| 2-Theta | d(A) | Height | Height % |
| --- | --- | --- | --- |
| 9.402 | 9.3985 | 185 | 54.9 |
| 11.082 | 7.9772 | 144 | 42.7 |
| 11.460 | 7.7152 | 307 | 91.1 |
| 12.004 | 7.3667 | 262 | 77.7 |
| 12.683 | 6.9738 | 236 | 69.7 |
| 13.290 | 6.6567 | 86 | 25.2 |
| 14.287 | 8.1942 | 138 | 40.9 |
| 15.549 | 5.6942 | 190 | 56.4 |
| 16.406 | 5.3988 | 298 | 88.4 |
| 17.209 | 5.1485 | 185 | 64.9 |
| 18.652 | 4.7532 | 187 | 56.5 |
| 19.367 | 4.5794 | 136 | 40.9 |
| 19.846 | 4.4698 | 112 | 33.2 |
| 20.145 | 4.4044 | 166 | 46.0 |
| 21.009 | 4.2261 | 316 | 53.5 |
| 21.367 | 4.1550 | 121 | 35.9 |
| 22.368 | 3.9713 | 151 | 44.8 |
| 23.051 | 3.8562 | 297 | 88.1 |
| 23.410 | 3.7969 | 337 | 100.0 |
| 24.172 | 3.6788 | 86 | 25.2 |
| 24.625 | 3.6267 | 62 | 18.4 |
| 25.570 | 3.4808 | 70 | 20.8 |
| 25.951 | 3.4306 | 110 | 32.6 |
| 26.228 | 3.3949 | 269 | 79.8 |
| 26.872 | 3.3150 | 150 | 44.6 |
| 27.768 | 3.2101 | 96 | 28.5 |
| 29.836 | 2.9922 | 117 | 34.7 |
| 30.898 | 2.8917 | 40 | 11.9 |
| 36.518 | 2.4585 | 38 | 11.3 |
| 38.074 | 2.3616 | 39 | 11.8 |

Example 3

Preparation of Ropinirole Pamoate at a 2:1 Molar Ratio of Ropinirole to Pamoic Acid from a Mixture of Ethanol, Water and PEG6000.

Figure 5:
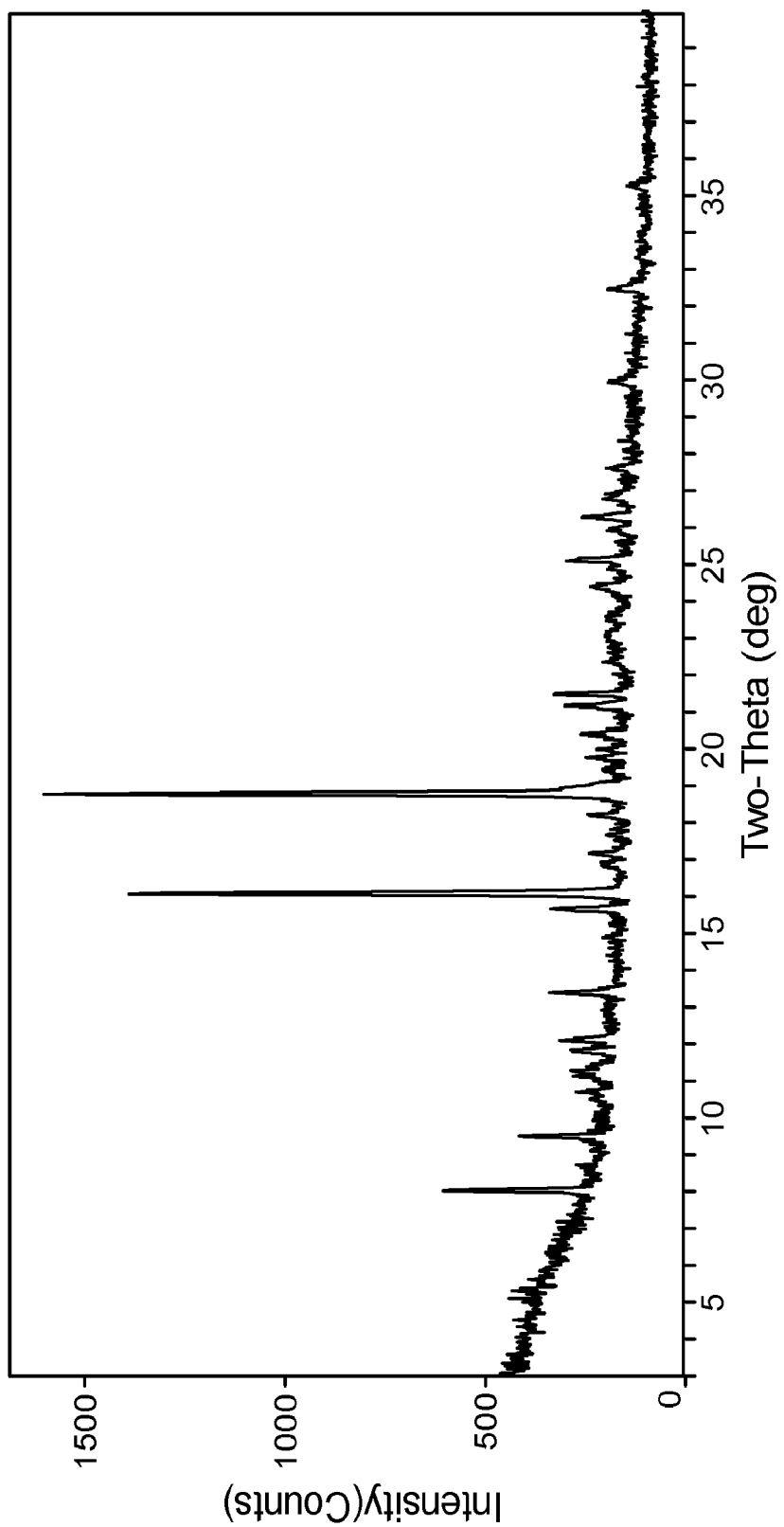
FIG. 5 depicts an XRPD spectrum of ropinirole pamoate Form C (2:1 molar ratio of ropinirole to pamoic acid) obtained from a mixture of ethanol, water and PEG6000.
Figure 6:
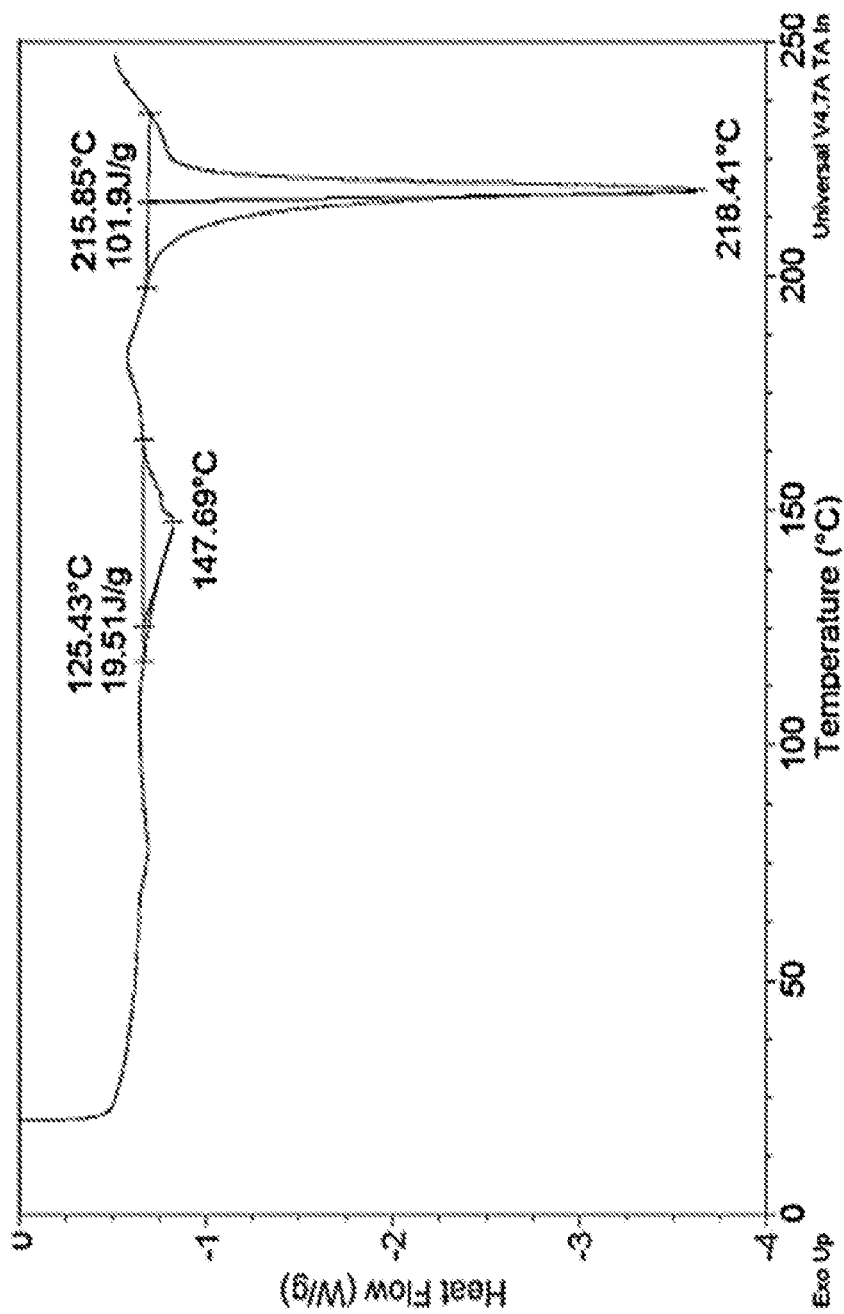
FIG. 6 depicts a DSC thermogram of ropinirole pamoate Form C (2:1 molar ratio of ropinirole to pamoic acid) obtained from a mixture of ethanol, water and PEG6000.
Figure 24:
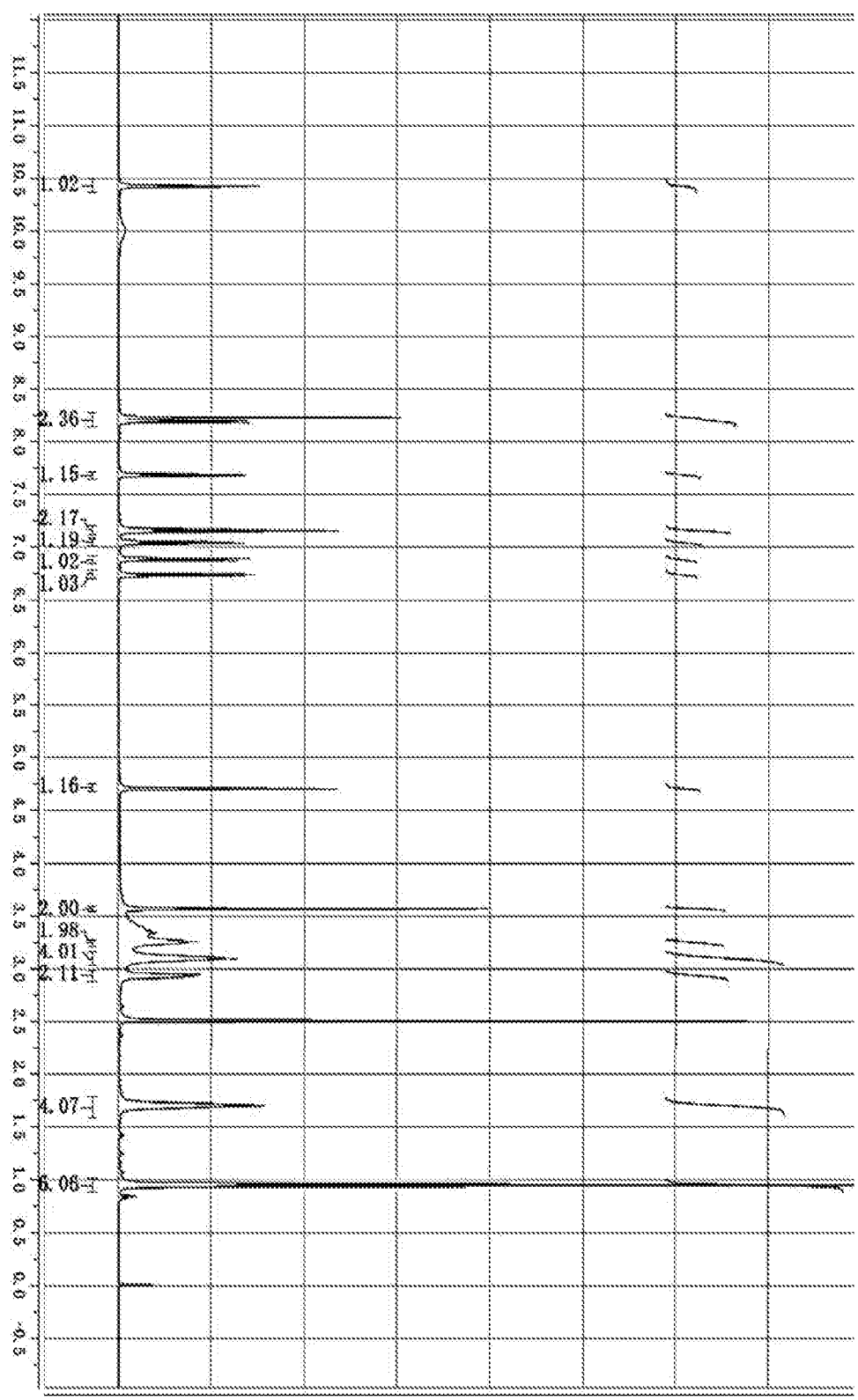
FIG. 24 depicts a $^1$H-NMR spectrum of Ropinirole pamoate (2:1 molar ratio of Ropinirole to pamoic acid) obtained from Example 3.

100 mg of ropinirole pamoate from Example 1 was dissolved at room temperature in a mixture of 14 mL of ethanol and 7 mL of water. To the solution was added 10% PEG6000 and the resultant mixture was dissolved by sonication which was then concentrated at 40° C., which produced a solid. This solid was then collected, washed, and dried. A typical example of an X-ray diffraction pattern for this solid is shown in FIG. 5 and Table 3. A typical example of a differential scanning calorimetry thermogram for this solid is shown in FIG. 6. $^1$H NMR (see FIG. 24) indicates that the molar ratio of Ropinirole to Pamoic Acid in the salt from Example 3 is about 2:1.

TABLE 3

| 2-Theta | d(A) | Height | Height % |
| --- | --- | --- | --- |
| 8.026 | 11.0074 | 362 | 24.9 |
| 9.501 | 3.3008 | 205 | 14.1 |
| 10.707 | 8.2559 | 71 | 4.9 |
| 11.275 | 7.8414 | 92 | 6.3 |
| 11.837 | 7.4700 | 96 | 6.6 |
| 12.103 | 7.3067 | 127 | 8.7 |
| 13.387 | 6.6084 | 186 | 11.4 |
| 15.666 | 5.6521 | 170 | 11.7 |
| 16.073 | 5.5097 | 1227 | 84.5 |
| 16.844 | 5.2591 | 50 | 3.4 |
| 17.166 | 8.1613 | 87 | 6.0 |
| 17.672 | 5.0147 | 46 | 3.3 |
| 18.219 | 4.8653 | 89 | 6.1 |
| 18.773 | 4.7229 | 1452 | 100.0 |
| 20.394 | 4.3611 | 94 | 5.5 |
| 21.158 | 4.1957 | 147 | 10.1 |
| 21.479 | 4.1396 | 177 | 12.2 |
| 22.359 | 3.9729 | 47 | 3.2 |

TABLE 3-continued

| 2-Theta | d(A) | Height | Height % |
| --- | --- | --- | --- |
| 23.852 | 3.8550 | 53 | 3.7 |
| 24.391 | 3.6463 | 78 | 5.4 |
| 25.100 | 3.5449 | 148 | 10.2 |
| 25.914 | 3.4354 | 64 | 3.7 |
| 26.277 | 3.3688 | 116 | 8.0 |
| 26.913 | 3.3101 | 60 | 4.1 |
| 27.813 | 3.2278 | 60 | 4.1 |
| 29.967 | 2.9794 | 68 | 4.7 |
| 32.473 | 2.7549 | 91 | 6.3 |
| 35.328 | 2.5385 | 45 | 3.1 |

Example 4

Preparation of Ropinirole Pamoate at a 1:1 Molar Ratio of Ropinirole to Pamoic Acid from a Mixture of DMSO and Acetonitrile.

Figure 7:
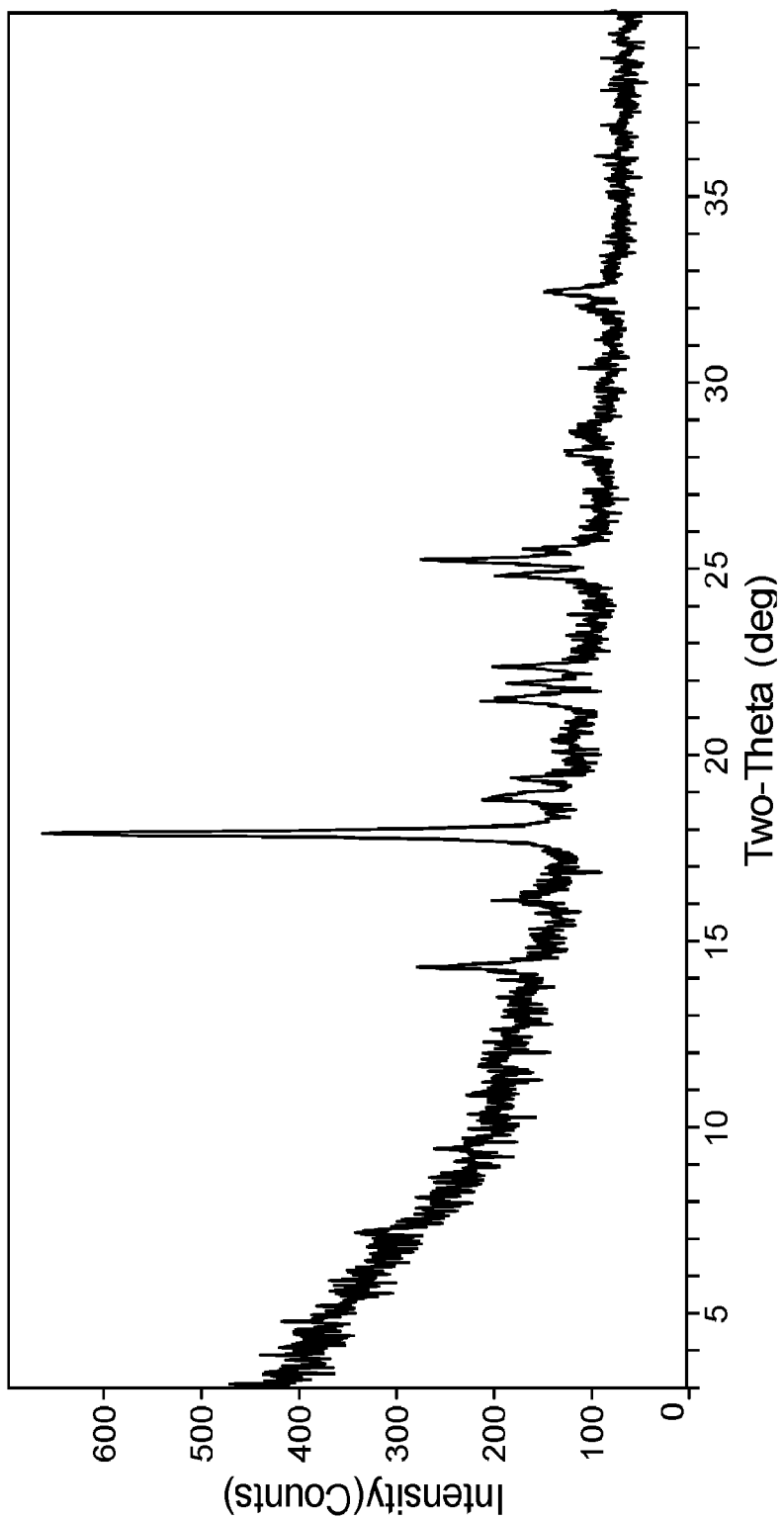
FIG. 7 depicts an XRPD spectrum of ropinirole pamoate Form D (1:1 molar ratio of ropinirole to pamoic acid) obtained from a mixture of DMSO and acetonitrile.
Figure 8:
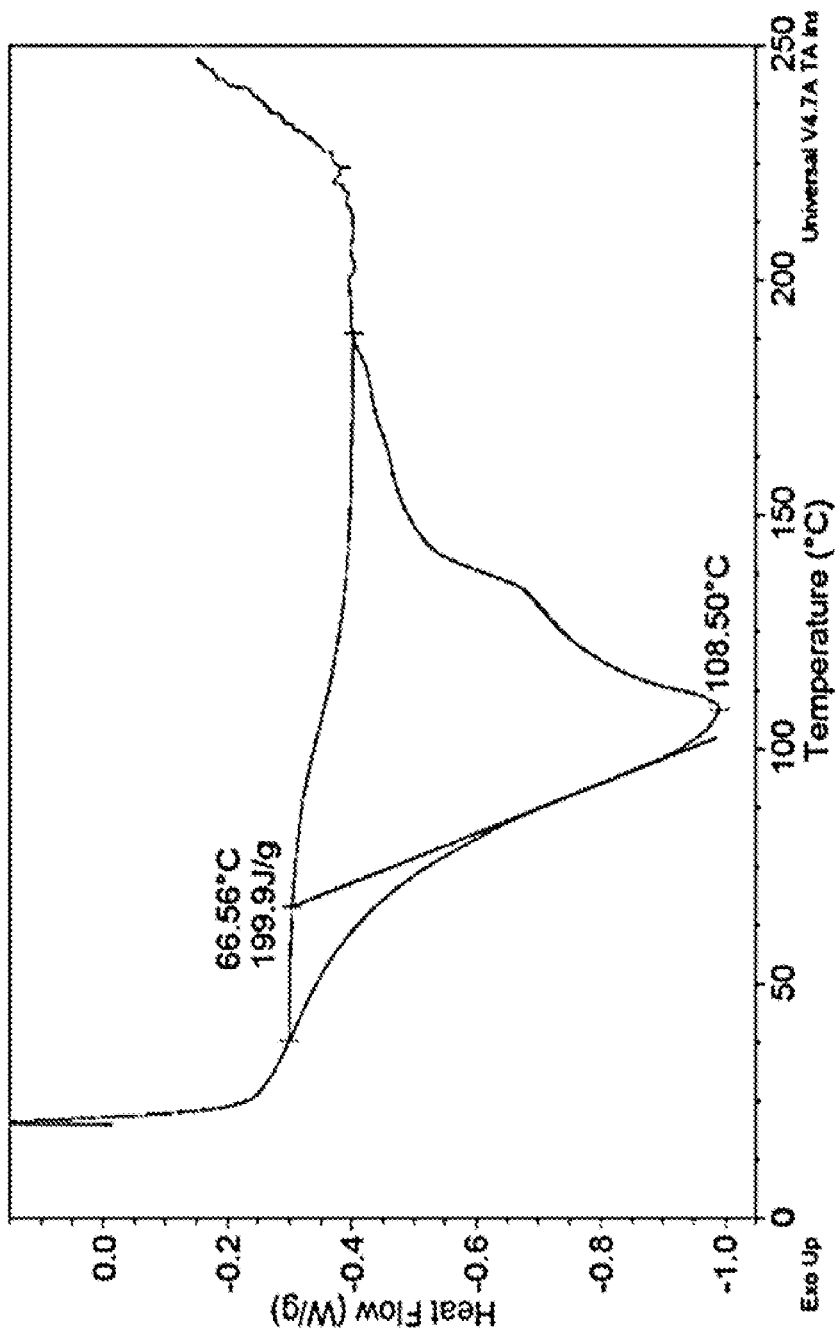
FIG. 8 depicts a DSC thermogram of ropinirole pamoate Form D (1:1 molar ratio of ropinirole to pamoic acid) obtained from a mixture of DMSO and acetonitrile.

100 mg of ropinirole pamoate from Example 1 was dissolved in 0.45 mL of dimethyl sulfoxide (DMSO). To the solution at room temperature was added 5 mL of acetonitrile. The resultant solution was then stirred at 4° C. to yield a solid, which was collected, washed, and dried. A typical example of an X-ray diffraction pattern for this solid is shown in FIG. 7 and Table 4. A typical example of a differential scanning calorimetry thermogram for this solid is shown in FIG. 8. $^1$H NMR indicates that the molar ratio of Ropinirole to Pamoic Acid in this solid is about 1:1.

TABLE 4

| 2-Theta | d(A) | Height | Height % |
| --- | --- | --- | --- |
| 9.426 | 9.3748 | 61 | 0.5 |
| 14.304 | 6.1866 | 129 | 24.0 |
| 16.106 | 5.4985 | 45 | 6.4 |
| 17.889 | 4.0544 | 538 | 100.0 |
| 18.846 | 4.7044 | 77 | 14.3 |
| 19.388 | 4.5760 | 59 | 11.0 |
| 21.453 | 4.1386 | 96 | 17.8 |
| 21.930 | 4.0496 | 65 | 12.1 |
| 22.370 | 3.9710 | 89 | 18.5 |
| 24.815 | 3.5860 | 102 | 10.0 |
| 25.248 | 3.5244 | 179 | 33.3 |
| 26.562 | 3.4819 | 56 | 10.4 |
| 28.168 | 3.1654 | 44 | 8.2 |
| 32.076 | 2.7881 | 39 | 7.2 |
| 32.436 | 2.7579 | 74 | 13.8 |

Example 5

Preparation of Ropinirole Pamoate at a 2:1 Molar Ratio of Ropinirole to Pamoic Acid from a Mixture of Ethanol, Water and Poly(Allylamine Hydrochloride).

Figure 9:
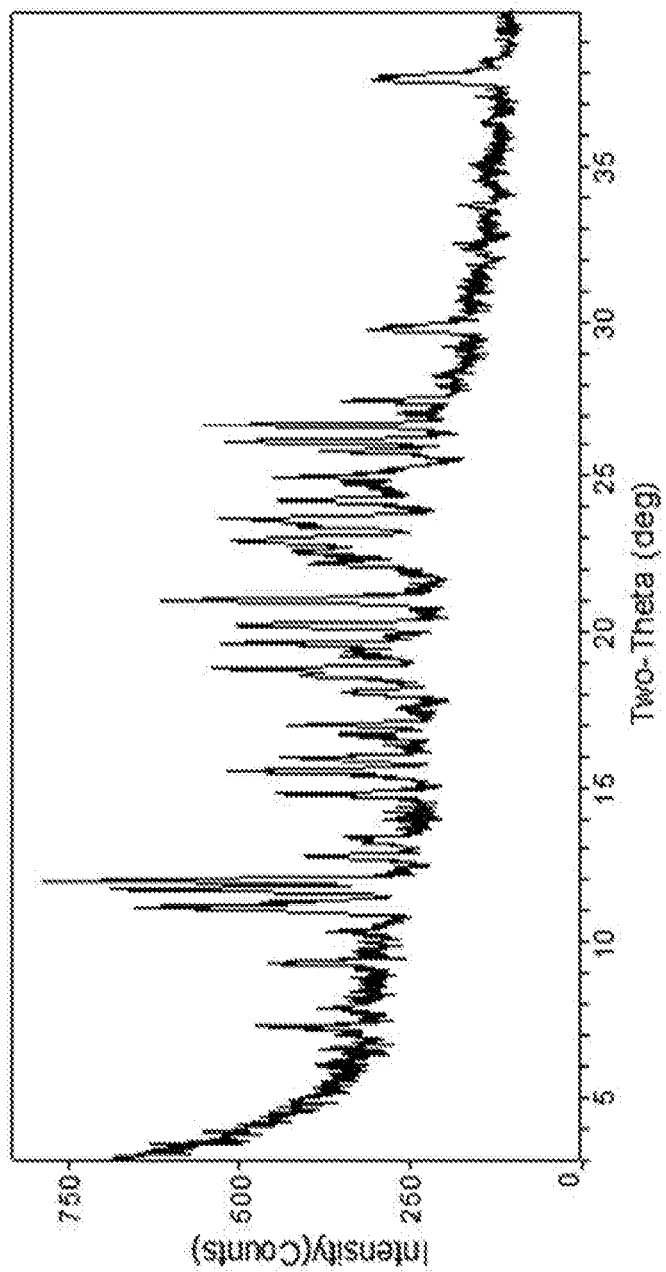
FIG. 9 depicts an XRPD spectrum of ropinirole pamoate Form E (2:1 molar ratio of ropinirole to pamoic acid) obtained from a mixture of ethanol, water and poly(allylamine hydrochloride).
Figure 10:
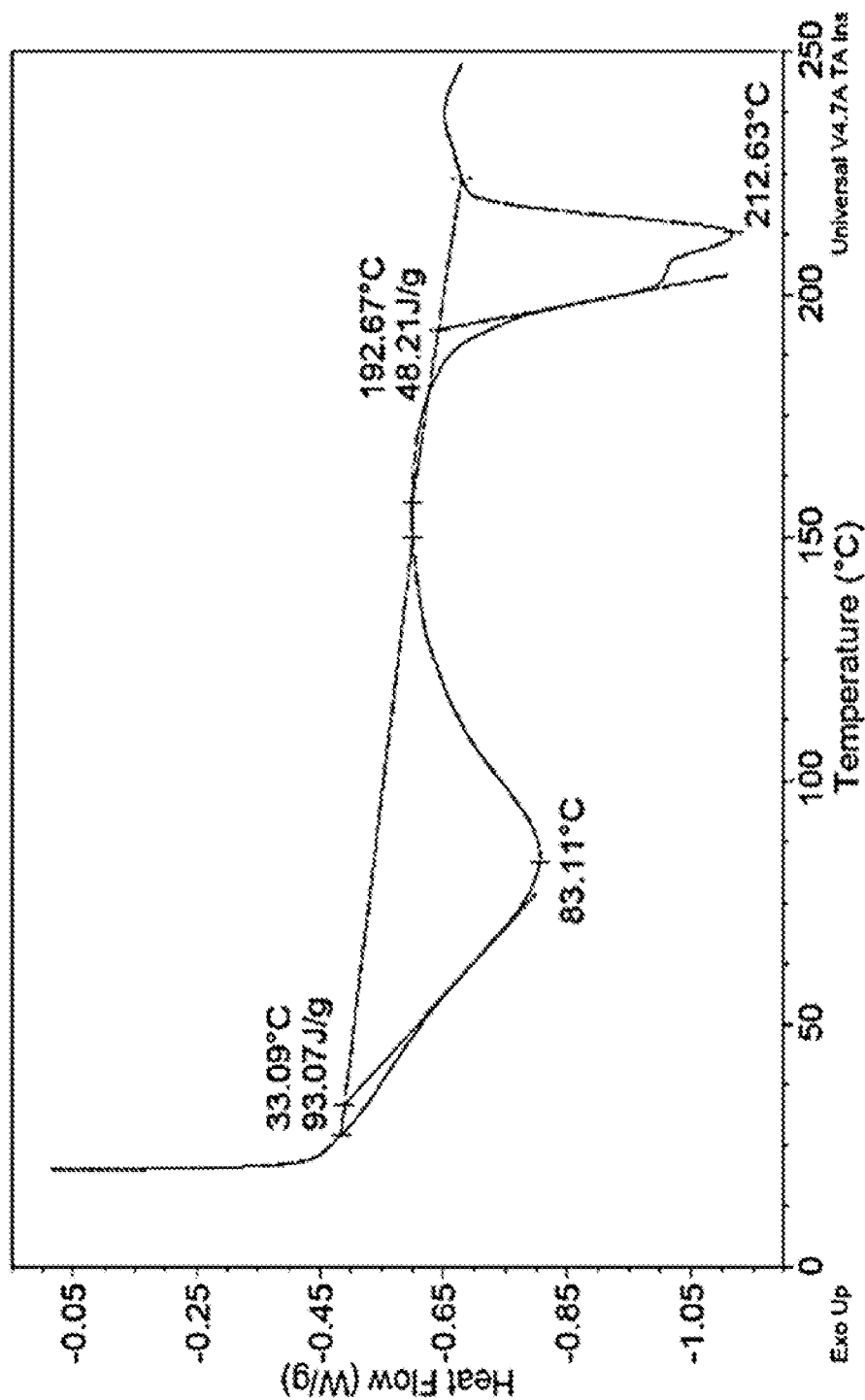
FIG. 10 depicts a DSC thermogram of ropinirole pamoate Form E (2:1 molar ratio of ropinirole to pamoic acid) obtained from a mixture of ethanol, water and poly(allylamine hydrochloride).

100 mg of ropinirole pamoate from Example 1 was dissolved in a mixture of 14 mL of ethanol and 7 mL of water. To the solution was added 10% poly(allylamine hydrochloride). After kept evaporation at 40° C., a solid was formed and characterized by XRPD and DSC. A typical example of an X-ray diffraction pattern for this solid is shown in FIG. 9 and Table 5. A typical example of a differential scanning calorimetry thermogram for this solid is shown in FIG. 10. $^1$H NMR indicates that the molar ratio of Ropinirole to Pamoic Acid in this solid is about 2:1.

TABLE 5

| 2-Theta | d(A) | Height | Height % |
|---|---|---|---|
| 7.281 | 12.1314 | 166 | 31.9 |
| 9.342 | 9.4591 | 159 | 30.5 |
| 10.346 | 8.5428 | 88 | 16.9 |
| 11.122 | 7.9400 | 365 | 70.1 |
| 11.685 | 7.5671 | 434 | 83.3 |
| 11.965 | 7.3905 | 521 | 100.0 |
| 12.783 | 6.9195 | 165 | 31.7 |
| 13.348 | 6.6279 | 99 | 19.0 |
| 14.800 | 5.9807 | 219 | 42.0 |
| 15.506 | 5.7099 | 289 | 55.5 |
| 15.948 | 5.5527 | 202 | 38.8 |
| 16.711 | 5.3007 | 122 | 23.4 |
| 16.992 | 5.2138 | 204 | 39.2 |
| 18.080 | 4.9024 | 109 | 20.9 |
| 18.807 | 4.7144 | 286 | 54.9 |
| 19.217 | 4.6149 | 95 | 18.2 |
| 19.612 | 4.5227 | 284 | 54.5 |
| 20.210 | 4.3902 | 260 | 49.9 |
| 21.009 | 4.2250 | 398 | 76.4 |
| 22.191 | 4.0027 | 165 | 31.7 |
| 22.571 | 3.9361 | 169 | 32.4 |
| 22.911 | 3.8785 | 267 | 51.2 |
| 23.629 | 3.7622 | 280 | 53.7 |
| 24.214 | 3.6726 | 185 | 35.5 |
| 24.691 | 3.6027 | 95 | 18.2 |
| 24.968 | 3.5633 | 199 | 38.2 |
| 25.791 | 3.4515 | 182 | 34.9 |
| 26.130 | 3.4075 | 320 | 61.4 |
| 26.636 | 3.3439 | 353 | 67.8 |
| 27.033 | 3.2957 | 77 | 14.8 |
| 27.458 | 3.2456 | 137 | 26.3 |
| 28.251 | 3.1563 | 46 | 8.8 |
| 29.223 | 3.0636 | 45 | 8.6 |
| 29.753 | 3.0003 | 150 | 28.8 |
| 32.523 | 2.7508 | 61 | 11.7 |
| 33.756 | 2.6530 | 61 | 11.7 |
| 34.561 | 2.5931 | 41 | 7.9 |
| 35.045 | 2.5584 | 50 | 9.6 |
| 37.818 | 2.3769 | 188 | 36.1 |
| 38.437 | 2.3400 | 38 | 7.3 |

Example 6

Preparation of Rotigotine Pamoate at a 1:1 Molar Ratio of Rotigotine to Pamoic Acid from a Mixture of Ethanol, Acetone, and n-Heptane.

Figure 11:
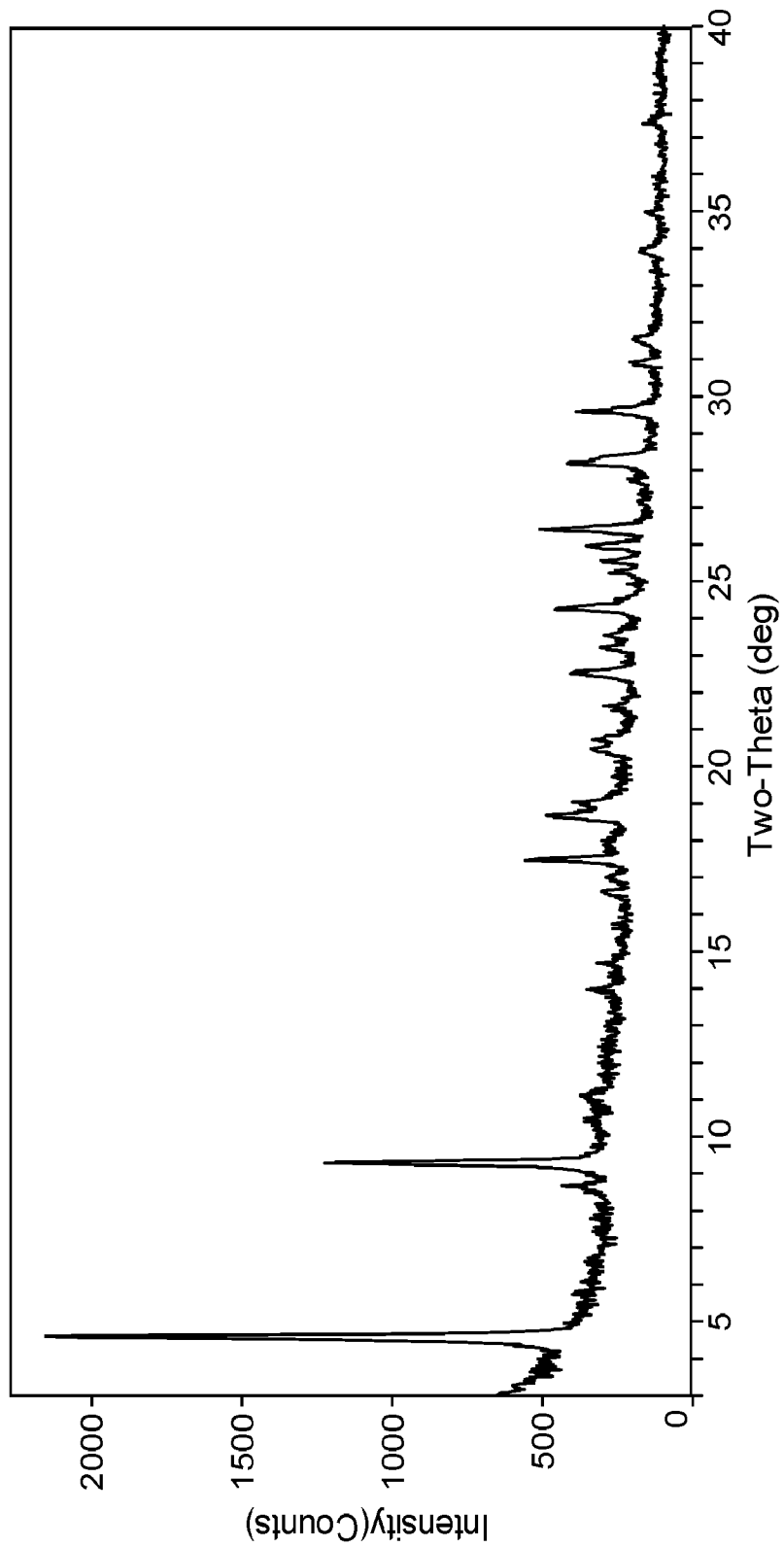
FIG. 11 depicts an XRPD spectrum of rotigotine pamoate Form I (1:1 molar ratio of rotigotine to pamoic acid) obtained from a mixture of ethanol, acetone, and n-heptane.
Figure 12:
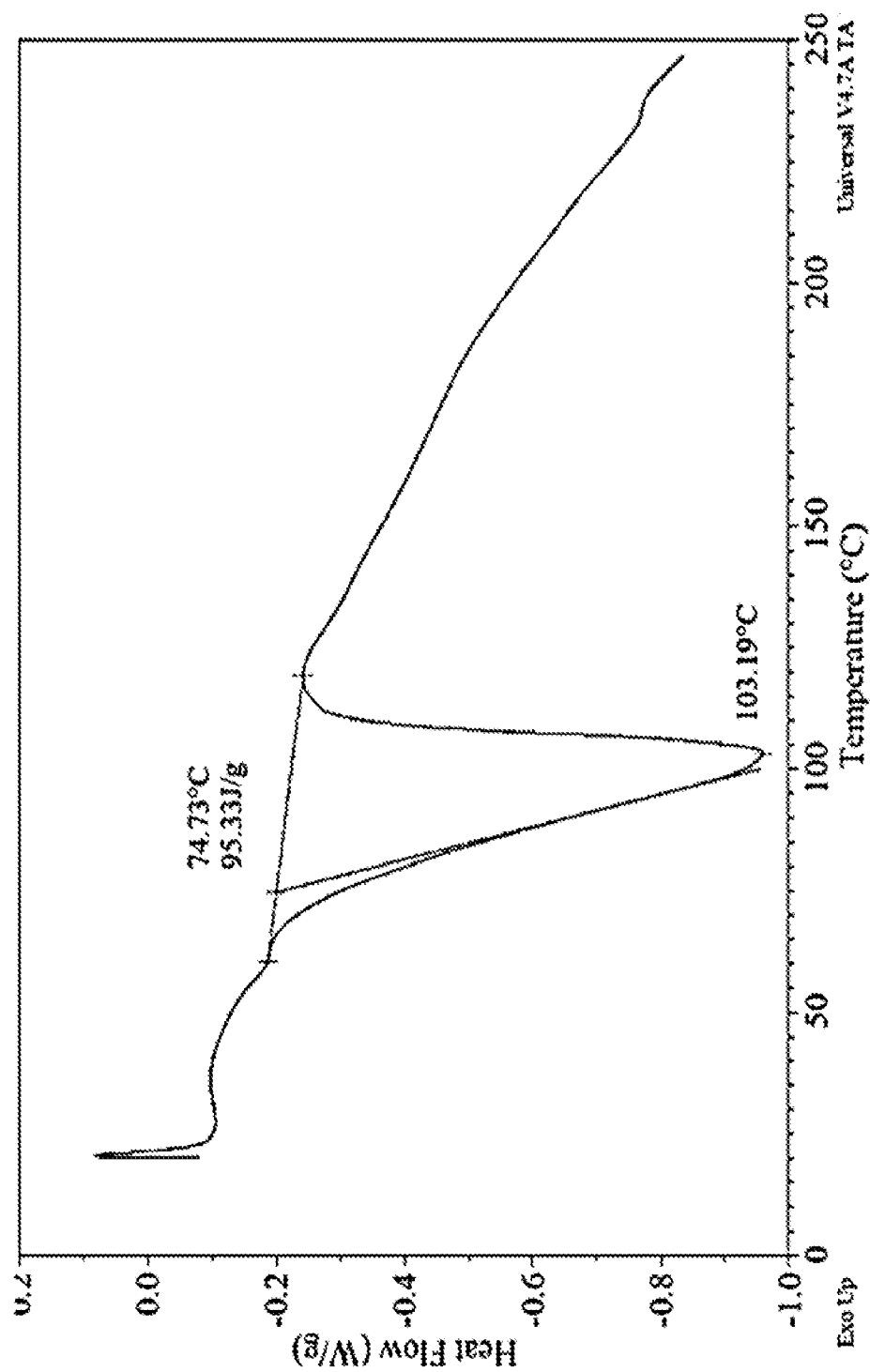
FIG. 12 depicts a DSC thermogram of rotigotine pamoate Form I (1:1 molar ratio of rotigotine to pamoic acid) obtained from a mixture of ethanol, acetone, and n-heptane.
Figure 25:
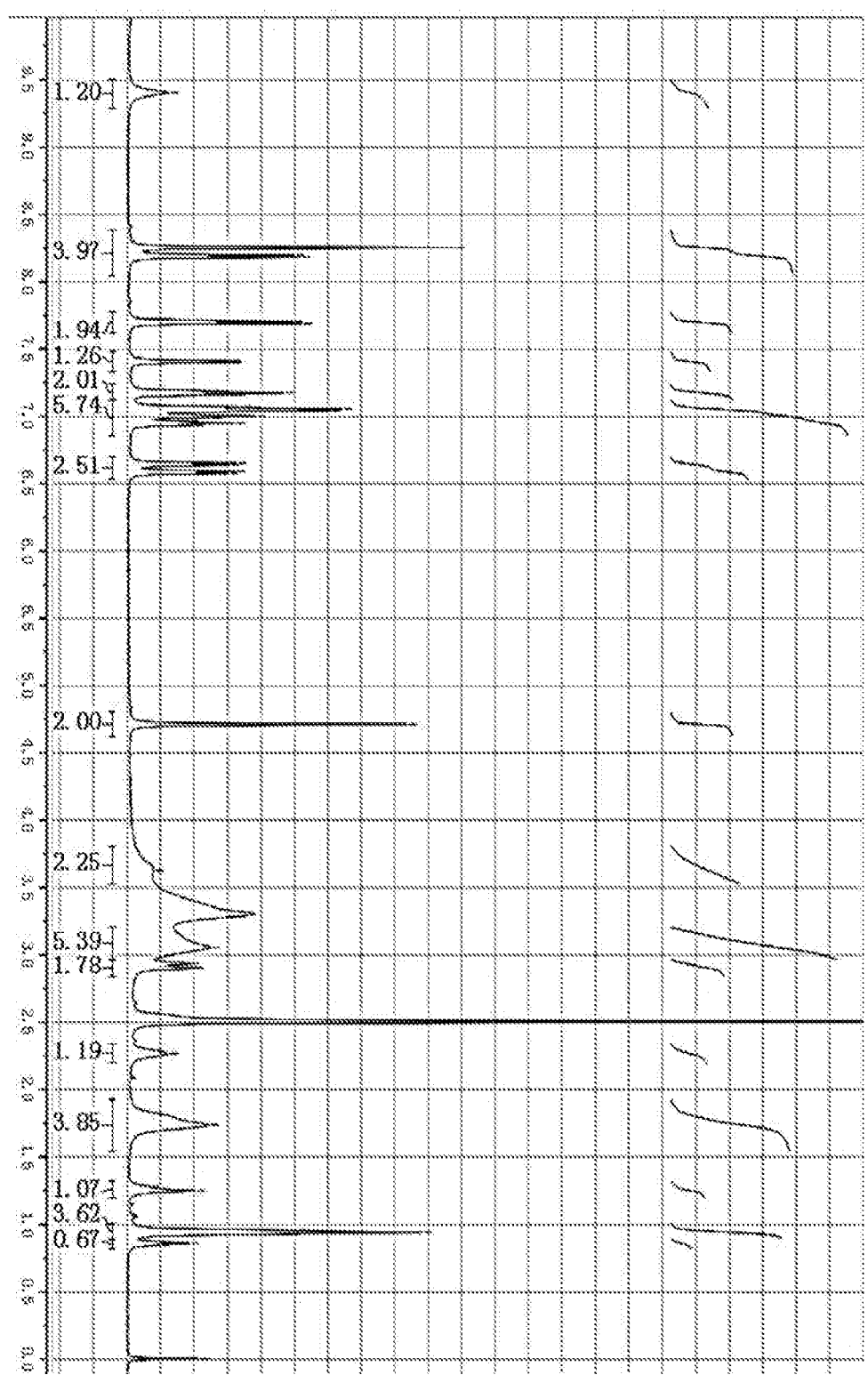
FIG. 25 depicts a $^1$H-NMR spectrum of Rotigotine pamoate (1:1 molar ratio of Rotigotine to Pamoic acid) obtained from Example 6.

35.2 mg of rotigotine hydrochloride salt was dissolved in a mixture of 4 mL of acetone and 1 mL of ethanol via sonication. Separately, 41 mg of sodium pamoate was dissolved in a mixture of 2 mL of ethanol and 0.4 mL of acetone. To the rotigotine hydrochloride solution was added in a dropwise manner the sodium pamoate solution. After addition and stirred for 30 minutes, 4 mL of n-heptane was added and the resultant solution was stirred overnight to generate rotigotine pamoate as crystalline solid. The solid was collected, washed with water, dried under vacuum, and characterized by XRPD and DSC. A typical example of an X-ray diffraction pattern for this solid is shown in FIG. 11 and Table 6. A typical example of a differential scanning calorimetry thermogram for this solid is shown in FIG. 12. ¹H NMR (see FIG. 25) indicates that the molar ratio of Rotigotine to Pamoic acid in this solid is about 1:1.

TABLE 6

| 2-Theta | d(A) | Height | Height % |
|---|---|---|---|
| 4.600 | 19.1958 | 1736 | 100.0 |
| 8.674 | 10.1855 | 124 | 7.1 |
| 9.284 | 9.5181 | 935 | 53.9 |
| 10.499 | 8.4193 | 68 | 3.9 |
| 11.105 | 7.9608 | 85 | 4.9 |
| 13.986 | 6.3274 | 106 | 6.0 |
| 14.678 | 6.0301 | 78 | 4.5 |
| 16.619 | 5.3298 | 71 | 4.1 |
| 17.000 | 5.2113 | 55 | 3.2 |
| 17.468 | 5.0728 | 321 | 18.6 |
| 17.883 | 4.9559 | 58 | 3.3 |
| 18.681 | 4.7459 | 251 | 14.5 |
| 19.040 | 4.6572 | 166 | 9.6 |
| 20.480 | 4.3330 | 121 | 7.0 |
| 20.722 | 4.2829 | 118 | 6.8 |
| 21.641 | 4.1031 | 94 | 5.4 |
| 22.506 | 3.9473 | 199 | 11.5 |
| 23.220 | 3.8275 | 103 | 5.9 |
| 23.543 | 3.7757 | 96 | 5.5 |
| 24.248 | 3.6675 | 270 | 15.6 |
| 25.230 | 3.5269 | 95 | 5.5 |
| 25.556 | 3.4827 | 117 | 6.7 |
| 25.961 | 3.4293 | 189 | 10.9 |
| 26.403 | 3.3729 | 317 | 18.3 |
| 27.754 | 3.2116 | 71 | 4.1 |
| 28.186 | 3.1634 | 270 | 15.6 |
| 29.587 | 3.0167 | 257 | 14.8 |
| 30.919 | 2.8897 | 87 | 5.0 |
| 31.545 | 2.8338 | 73 | 4.2 |
| 33.903 | 2.6419 | 74 | 4.3 |
| 34.978 | 2.5631 | 56 | 3.2 |
| 37.465 | 2.3985 | 40 | 2.3 |

Example 7

Preparation of Pramipexole Pamoate at a 1:1 Molar Ratio of Pramipexole to Pamoic Acid from a Mixture of Acetone and Water.

Pramipexole (3.0 g, 14.1 mmol) and Pamoic acid (2.7 g, 7.0 mmol) was dissolved by stirring at room temperature in DMSO (30 mL). The solution was then slowly added to ethyl acetate (2 L) at room temperature to generate a white solid. The solid was collected on a filter and dried in vacuum at 45° C. to give an amorphous pramipexole pamoate at a 2:1 Molar ratio of Pramipexole to Pamoic acid (4.5 g, 78.6%).

Figure 13:
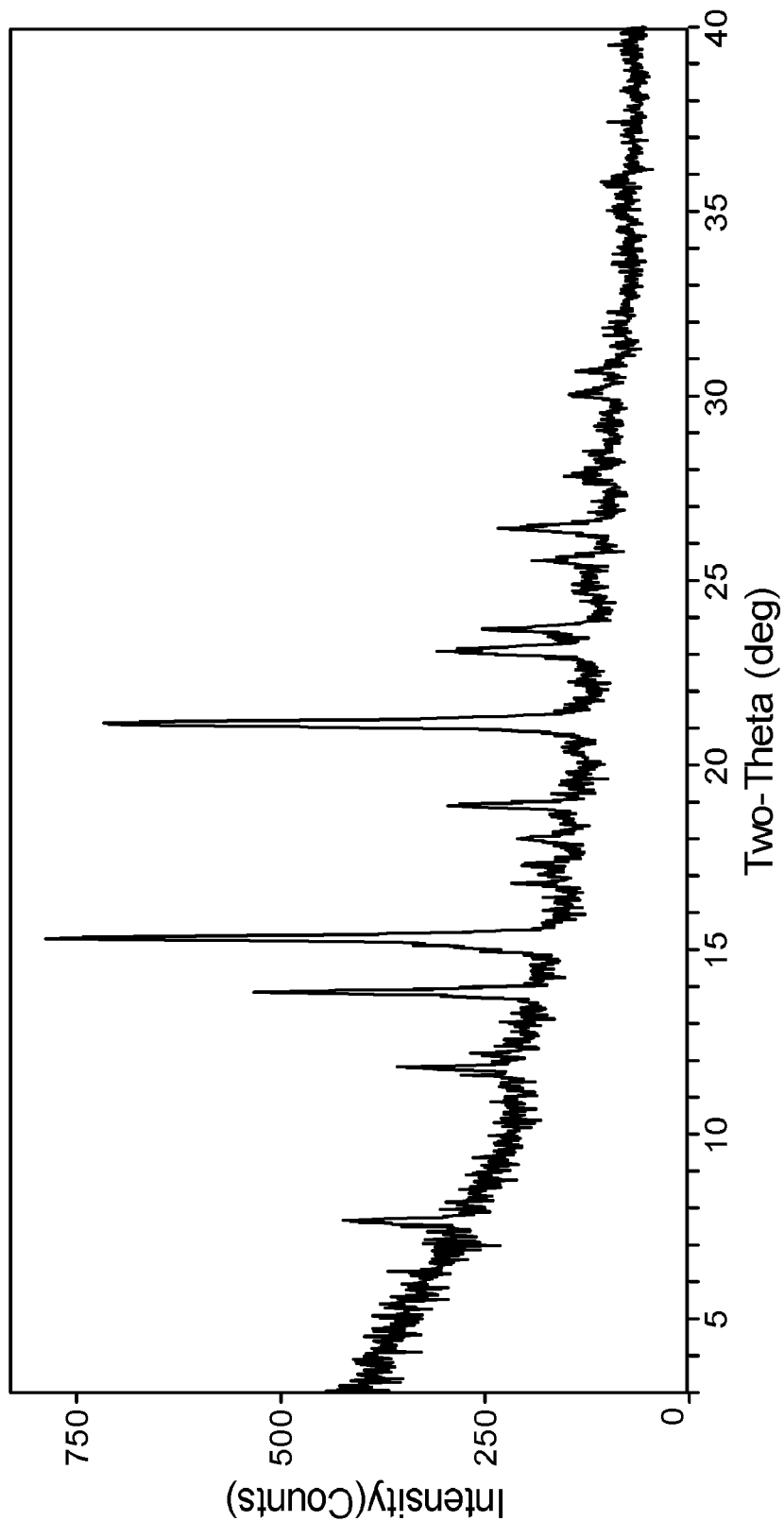
FIG. 13 depicts an XRPD spectrum of pramipexole pamoate Form 1 (1:1 molar ratio of pramipexole to pamoic acid) obtained from a mixture of acetone and water.
Figure 14:
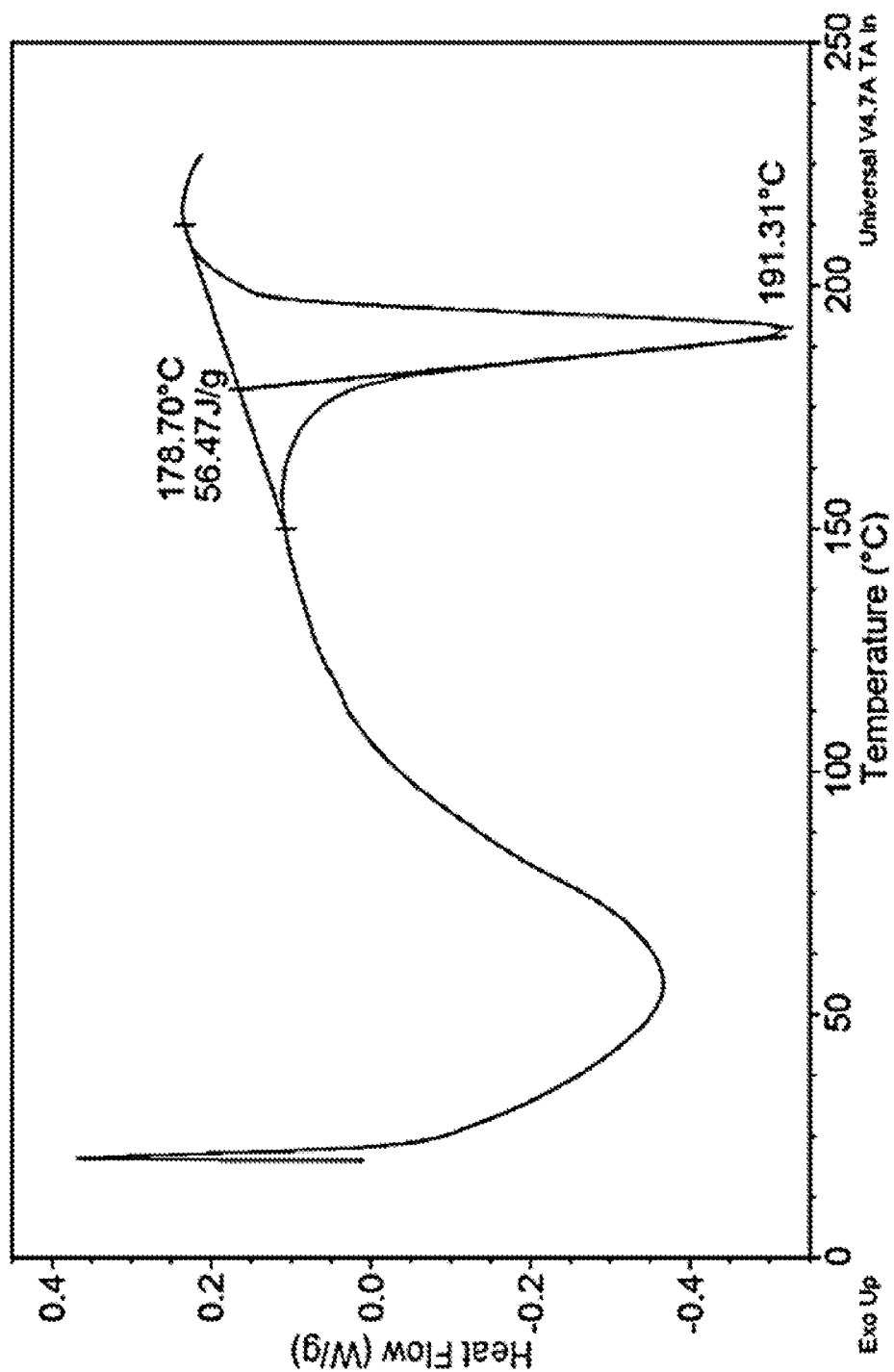
FIG. 14 depicts a DSC thermogram of pramipexole pamoate Form 1 (1:1 molar ratio of pramipexole to pamoic acid) obtained from a mixture of acetone and water.

100 mg of above amorphous pramipexole pamoate salt was dissolved in a mixture of 3 mL of acetone and 0.5 mL of water at 60° C. The solution was slowly cooled to room temperature and stirred for 3 hours to yield pramipexole pamoate as a solid, which was collected, washed, and dried. The solid was characterized by XRPD and DSC. A typical example of an X-ray diffraction pattern for this solid is shown in FIG. 13 and Table 7. A typical example of a differential scanning calorimetry thermogram for this solid is shown in FIG. 14. ¹H NMR (see FIG. 21) indicates that the molar ratio of Pramipexole to Pamoic acid in this solid is about 1:1.

TABLE 7

| 2-Theta | d(A) | Height | Height % |
|---|---|---|---|
| 7.659 | 11.5328 | 153 | 24.2 |
| 11.817 | 7.4826 | 157 | 24.8 |
| 12.130 | 7.2905 | 56 | 8.9 |
| 13.843 | 6.3920 | 354 | 56.0 |
| 15.303 | 5.7852 | 632 | 100.0 |
| 16.796 | 5.2741 | 72 | 11.4 |
| 17.285 | 5.1259 | 64 | 10.1 |
| 18.020 | 4.9186 | 64 | 10.1 |
| 18.903 | 4.6906 | 159 | 25.2 |
| 21.141 | 4.1989 | 595 | 94.1 |

TABLE 7-continued

| 2-Theta | d(A) | Height | Height % |
|---|---|---|---|
| 23.082 | 3.8502 | 194 | 30.7 |
| 23.680 | 3.7541 | 136 | 21.5 |
| 25.542 | 3.4846 | 83 | 13.1 |
| 26.421 | 3.3706 | 136 | 21.4 |
| 27.904 | 3.1948 | 50 | 7.9 |
| 30.109 | 2.9656 | 52 | 8.2 |
| 30.682 | 2.9115 | 53 | 8.4 |

Example 8

Preparation of Pramipexole Pamoate at a 1:1 Molar Ratio of Pramipexole to Pamoic Acid from a Mixture of Acetone and Methanol.

Figure 15:
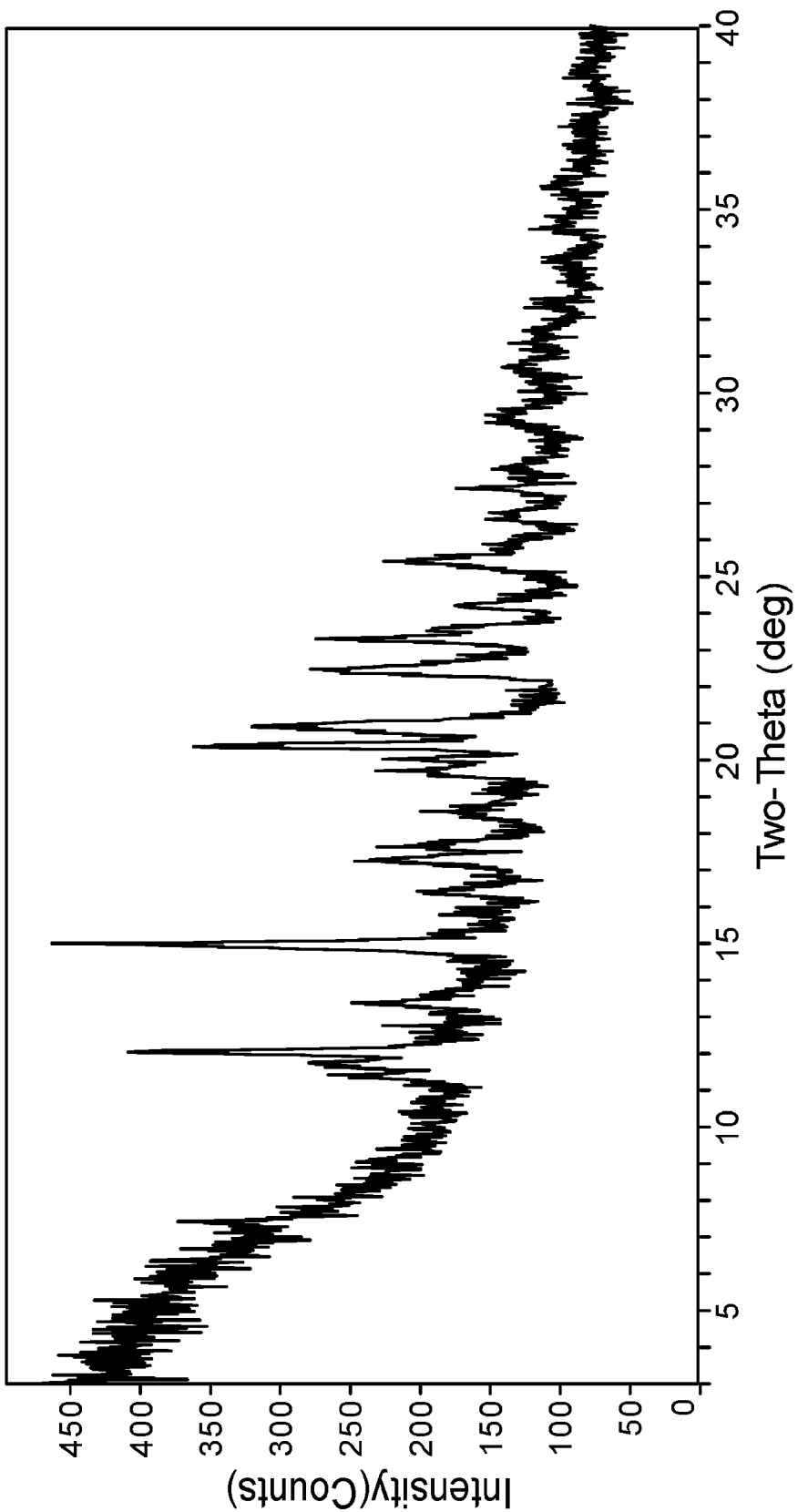
FIG. 15 depicts an XRPD spectrum of pramipexole pamoate Form 2 (1:1 molar ratio of pramipexole to pamoic acid) obtained from a mixture of acetone and methanol.
Figure 16:
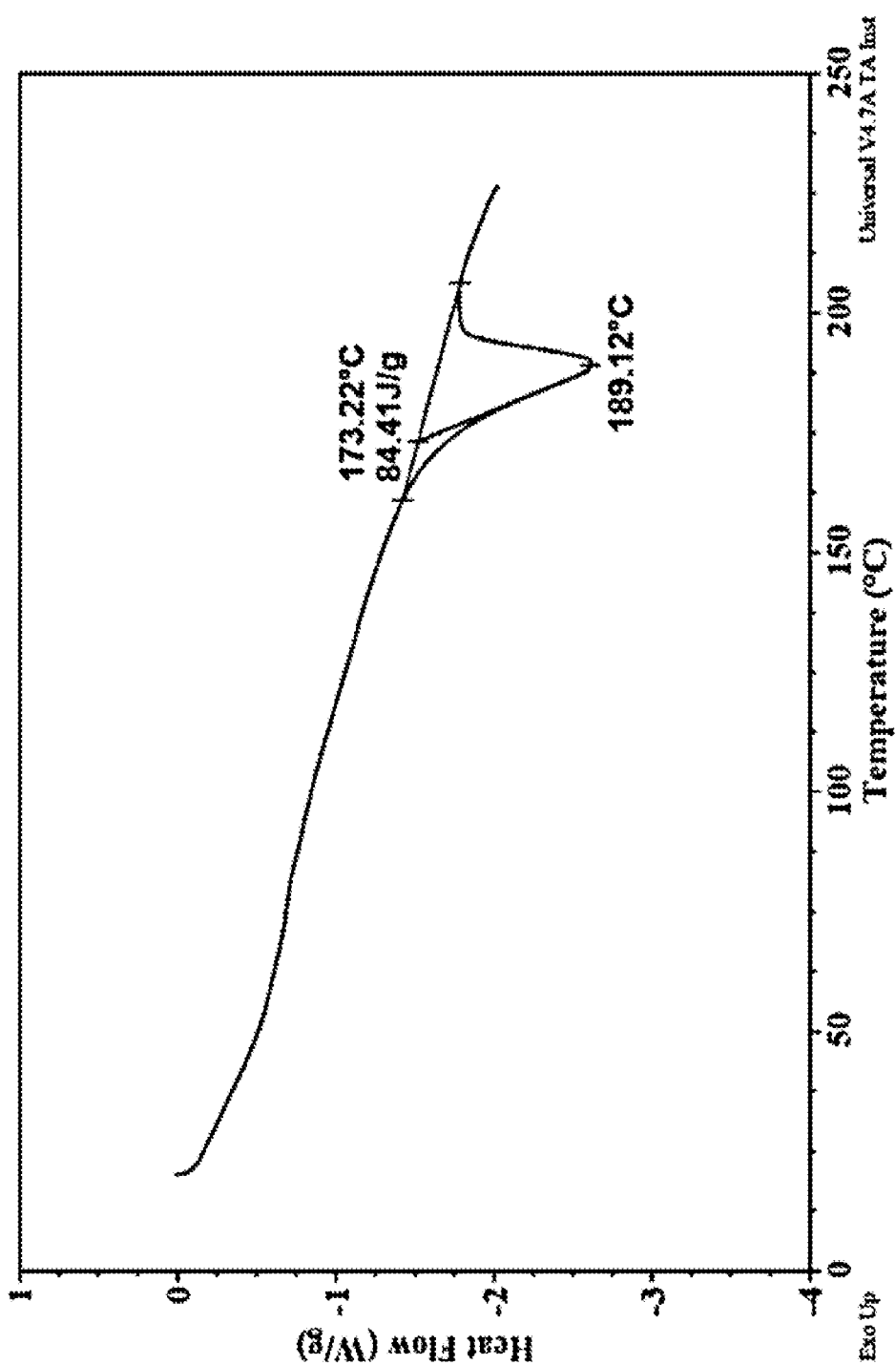
FIG. 16 depicts a DSC thermogram of pramipexole pamoate Form 2 (1:1 molar ratio of pramipexole to pamoic acid) obtained from a mixture of acetone and methanol.

100 mg of amorphous pramipexole pamoate salt from Example 7 was dissolved in 0.6 mL of methanol at room temperature. To the solution was added 3 mL of acetone with stirring to yield pramipexole pamoate as a crystalline solid, which was collected, washed, and dried. The solid was characterized by XRPD and DSC. A typical example of an X-ray diffraction pattern for this solid is shown in FIG. 15 and Table 8. A typical example of a differential scanning calorimetry thermogram for this solid is shown in FIG. 16. $^1$H NMR indicates that the molar ratio of Pramipexole to Pamoic acid in this solid is about 1:1.

TABLE 8

| 2-Theta | d(A) | Height | Height % |
|---|---|---|---|
| 7.416 | 11.9106 | 86 | 26.8 |
| 11.421 | 7.7416 | 67 | 27.4 |
| 11.740 | 7.5317 | 100 | 31.5 |
| 12.043 | 7.3428 | 238 | 74.1 |
| 13.378 | 6.6126 | 83 | 26.2 |
| 14.999 | 5.9018 | 317 | 100.0 |
| 16.417 | 5.3949 | 69 | 21.8 |
| 17.243 | 5.1383 | 115 | 36.3 |
| 17.696 | 5.0074 | 71 | 22.4 |
| 18.595 | 4.7677 | 72 | 22.7 |
| 19.704 | 4.5017 | 93 | 29.3 |
| 20.022 | 4.4310 | 79 | 24.9 |
| 20.364 | 4.3574 | 239 | 75.4 |
| 20.905 | 4.2459 | 186 | 89.3 |
| 22.480 | 3.9518 | 151 | 47.6 |
| 23.302 | 3.8143 | 149 | 47.0 |
| 23.579 | 3.7701 | 65 | 20.5 |
| 24.202 | 3.6743 | 68 | 21.5 |
| 25.424 | 3.5005 | 123 | 38.8 |
| 25.861 | 3.4397 | 47 | 14.8 |
| 27.406 | 3.2517 | 69 | 18.6 |
| 29.398 | 3.0357 | 50 | 15.8 |
| 31.368 | 2.8494 | 37 | 11.7 |
| 33.712 | 2.6564 | 34 | 10.7 |
| 34.525 | 2.5957 | 34 | 10.7 |

Example 9

Preparation of Pramipexole Pamoate at a 2:1 Molar Ratio of Pramipexole to Pamoic Acid from a Solution of Ethyl Acetate.

Figure 17:
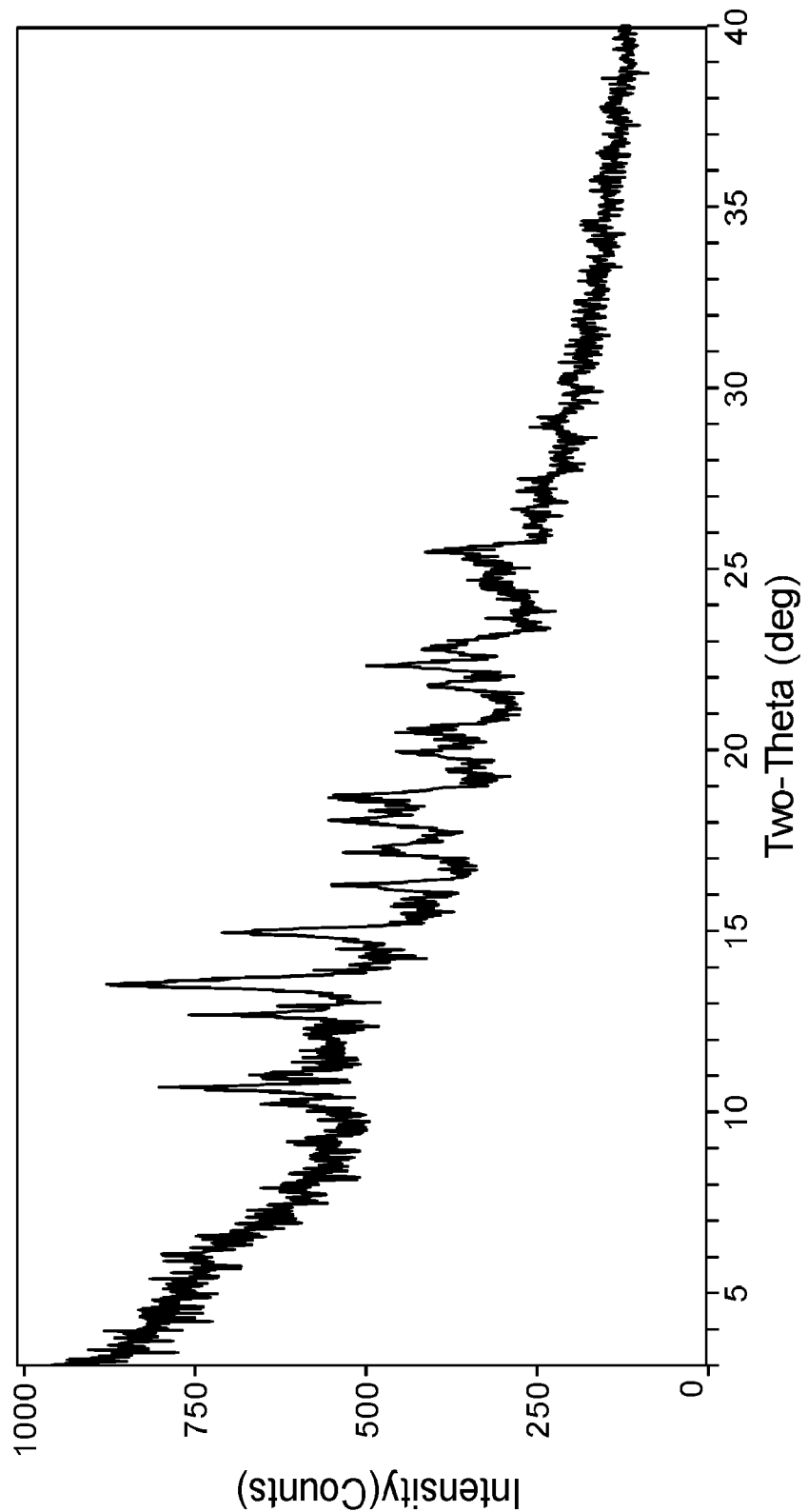
FIG. 17 depicts an XRPD spectrum of pramipexole pamoate Form 3 (2:1 molar ratio of pramipexole to pamoic acid) obtained from a solution of ethyl acetate.
Figure 18:
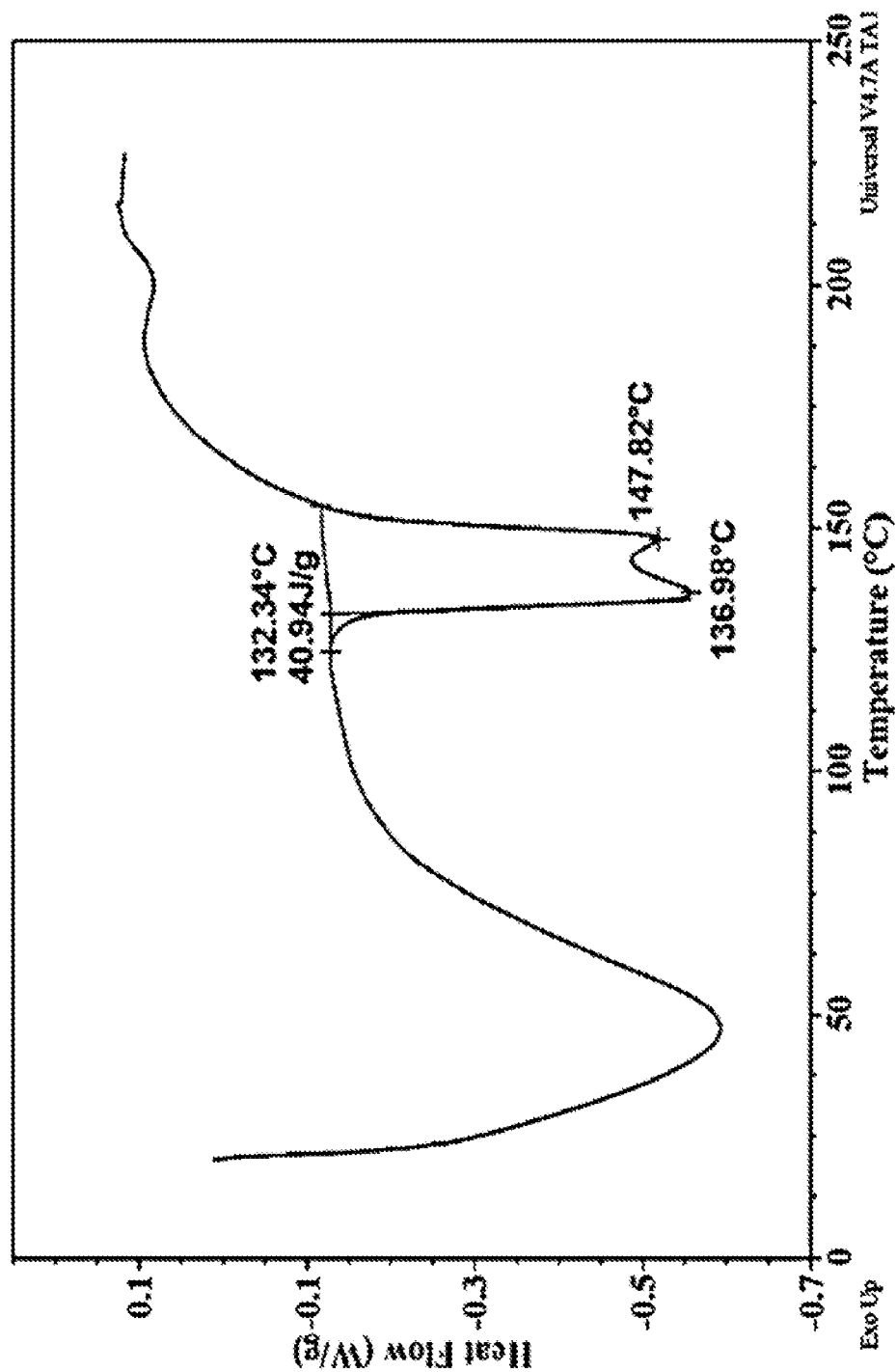
FIG. 18 depicts a DSC thermogram of pramipexole pamoate Form 3 (2:1 molar ratio of pramipexole to pamoic acid) obtained from a solution of ethyl acetate.
Figure 26:
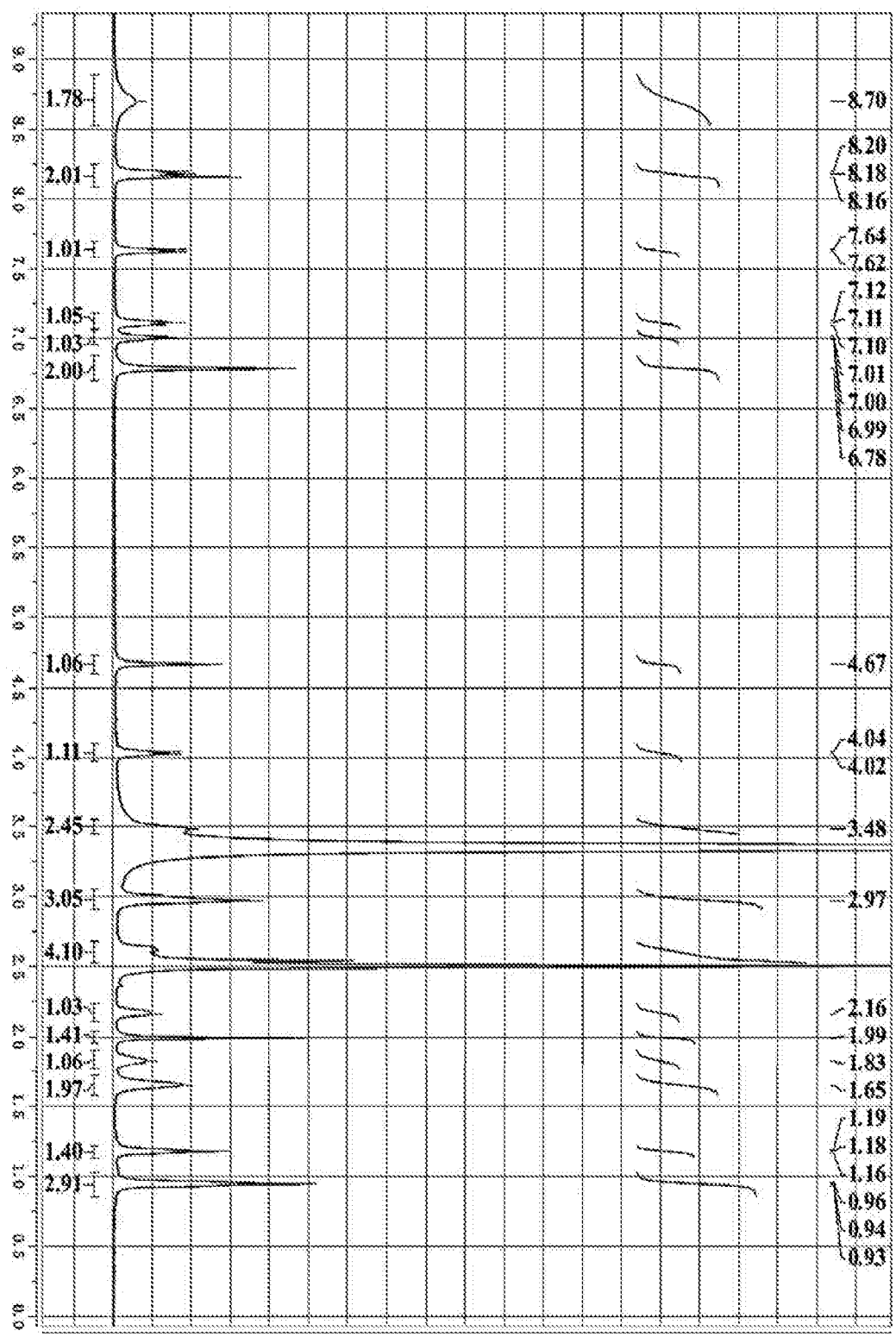
FIG. 26 depicts a $^1$H-NMR spectrum of pramipexole pamoate (2:1 molar ratio of pramipexole to pamoic acid) obtained from Example 9.

50 mg of amorphous pramipexole pamoate salt from Example 7 was dissolved in 2.5 mL of ethyl acetate. The solution was stirred for 5 days at room temperature to yield pramipexole pamoate as a solid, which was collected, washed, and dried. The solid was characterized by XRPD and DSC. A typical example of an X-ray diffraction pattern for this solid is shown in FIG. 17 and Table 9. A typical example of a differential scanning calorimetry thermogram for this solid is shown in FIG. 18. $^1$H NMR (see FIG. 26) indicates that the molar ratio of Pramipexole to Pamoic acid in this solid is about 2:1.

TABLE 9

| 2-Theta | d(A) | Height | Height % |
|---|---|---|---|
| 6.051 | 14.5950 | 100 | 28.2 |
| 9.181 | 0.6241 | 81 | 21.2 |
| 10.227 | 8.6423 | 100 | 26.2 |
| 10.681 | 8.2760 | 281 | 68.3 |
| 11.018 | 8.0235 | 112 | 29.3 |
| 12.683 | 6.9735 | 225 | 58.9 |
| 13.523 | 6.5426 | 382 | 100.0 |
| 14.942 | 6.9241 | 277 | 72.6 |
| 16.276 | 6.4418 | 166 | 43.5 |
| 17.243 | 5.1385 | 101 | 26.4 |
| 18.062 | 4.9073 | 183 | 47.9 |
| 18.681 | 4.7400 | 207 | 54.2 |
| 19.957 | 4.4454 | 138 | 36.1 |
| 20.483 | 4.3324 | 143 | 37.4 |
| 21.780 | 4.0771 | 95 | 24.9 |
| 22.325 | 3.9790 | 212 | 55.5 |
| 22.788 | 3.9028 | 134 | 35.1 |
| 23.644 | 3.7598 | 66 | 17.3 |
| 24.820 | 3.5843 | 73 | 19.1 |
| 25.566 | 3.4814 | 106 | 27.7 |
| 27.479 | 3.2432 | 56 | 14.7 |
| 28.000 | 3.0868 | 68 | 17.8 |

Example 10

Figure 19:
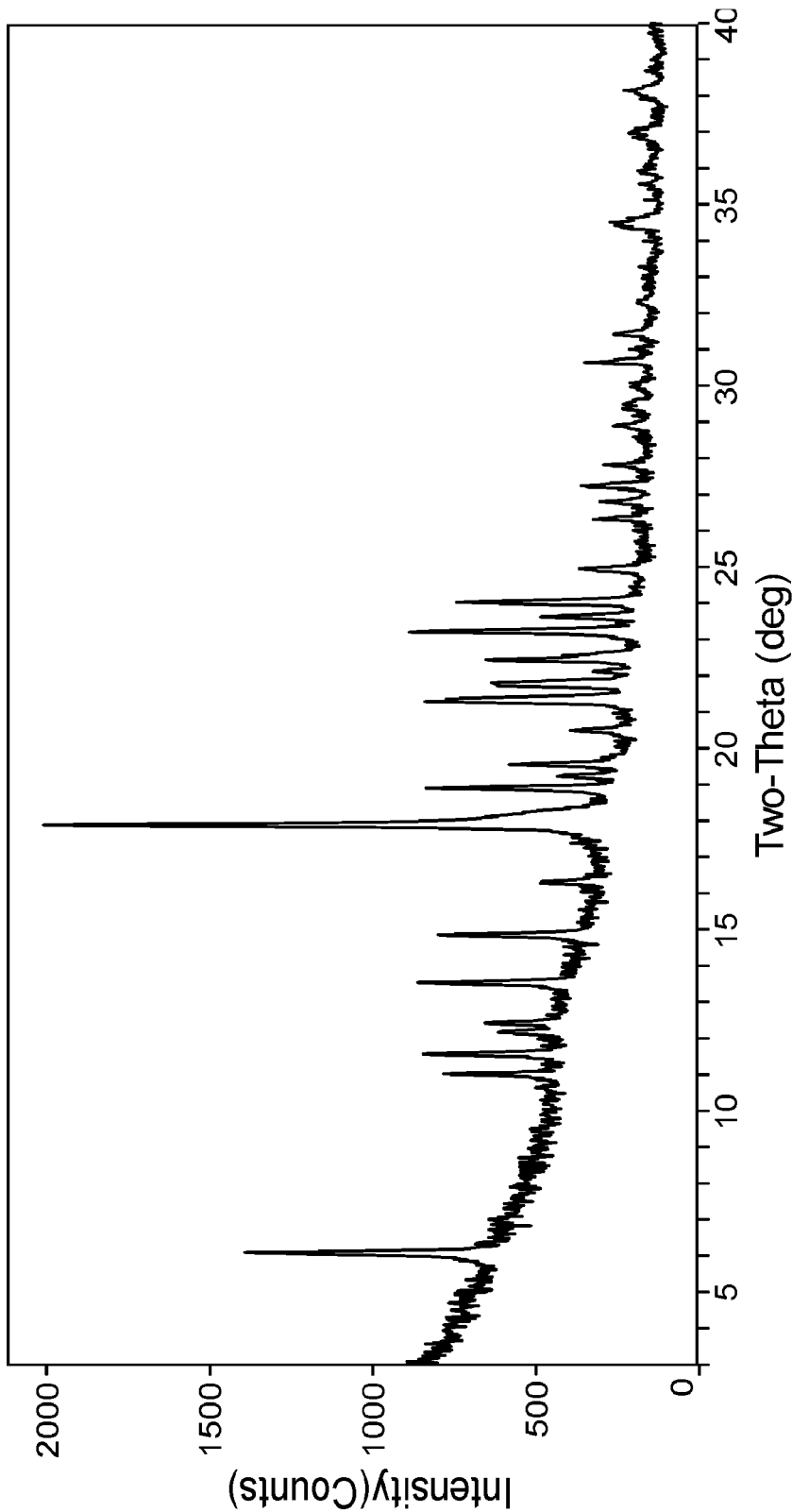
FIG. 19 depicts an XRPD spectrum of pramipexole pamoate Form 4 (2:1 molar ratio of pramipexole to pamoic acid) obtained from a solution of tetrahydrofuran.
Figure 20:
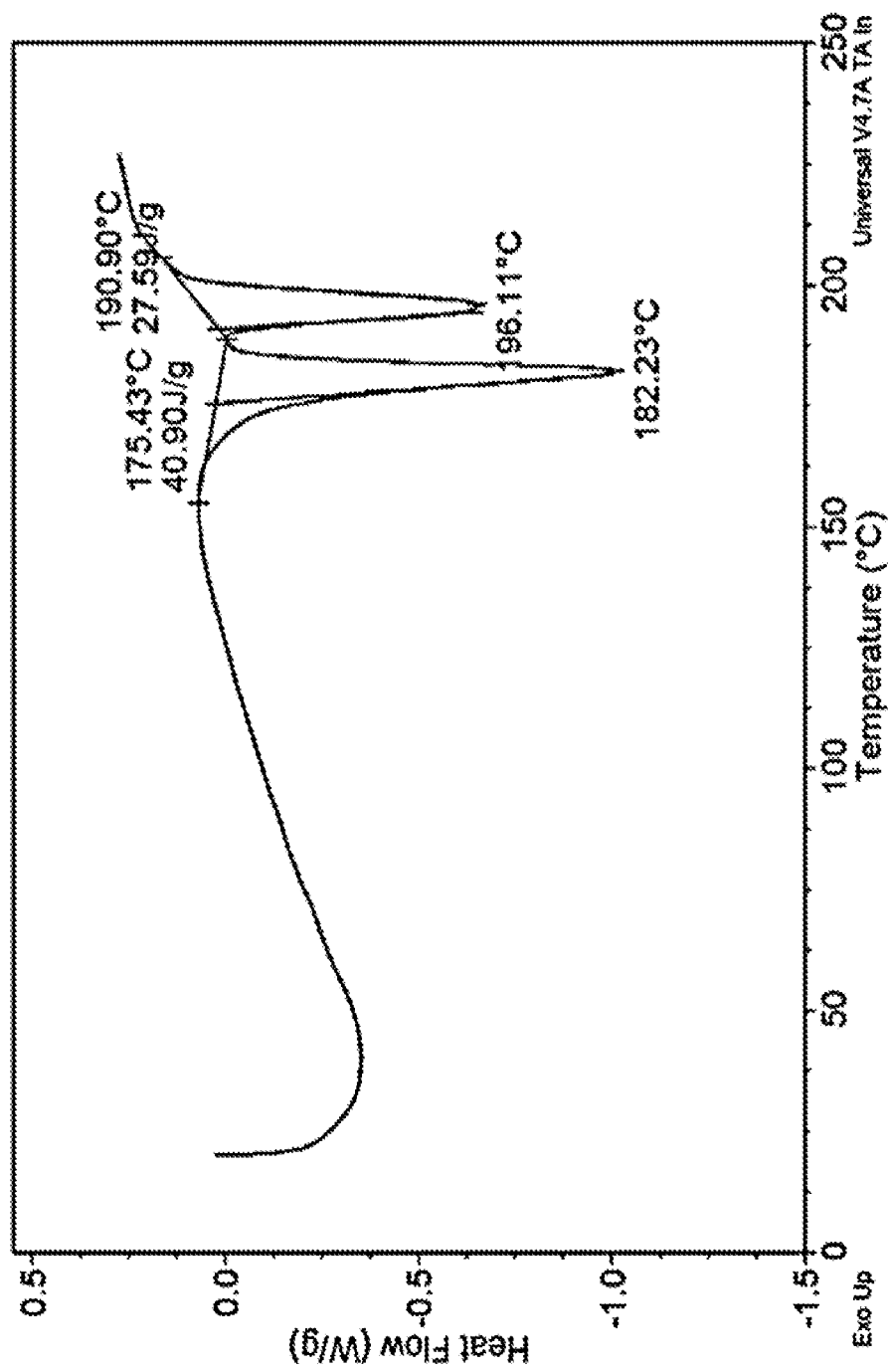
FIG. 20 depicts a DSC thermogram of pramipexole pamoate Form 4 (2:1 molar ratio of pramipexole to pamoic acid) obtained from a solution of tetrahydrofuran.

Preparation of Pramipexole Pamoate at a 2:1 Molar Ratio of Pramipexole to Pamoic Acid from a Solution of Tetrahydrofuran 50 mg of amorphous pramipexole pamoate salt from Example 7 was dissolved in 2.5 mL of tetrahydrofuran (THF). The solution was stirred for 10 days at room temperature to yield pramipexole pamoate as a solid, which was collected, washed, and dried. The solid was characterized by XRPD and DSC. A typical example of an X-ray diffraction pattern for this solid is shown in FIG. 19 and Table 10. A typical example of a differential scanning calorimetry thermogram for this solid is shown in FIG. 20. $^1$H NMR (see FIG. 22) indicates that the molar ratio of Pramipexole to Pamoic acid in this solid is about 2:1.

TABLE 10

| 2-Theta | d(A) | Height | Height % |
|---|---|---|---|
| 6.096 | 14.4875 | 773 | 45.0 |
| 11.018 | 8.0238 | 341 | 19.9 |
| 11.563 | 7.8489 | 400 | 23.3 |
| 12.164 | 7.2701 | 177 | 10.3 |
| 12.421 | 7.1200 | 221 | 12.9 |
| 13.539 | 6.5348 | 458 | 28.7 |
| 14.856 | 5.9582 | 449 | 28.2 |
| 16.289 | 5.4373 | 167 | 9.7 |
| 17.883 | 4.9559 | 1717 | 100.0 |
| 18.903 | 4.8908 | 558 | 32.5 |
| 19.227 | 4.8125 | 141 | 8.2 |
| 19.456 | 4.5379 | 313 | 18.2 |
| 20.500 | 4.3288 | 176 | 10.2 |
| 21.286 | 4.1707 | 617 | 35.9 |
| 21.799 | 4.0736 | 425 | 24.8 |
| 22.441 | 3.9586 | 428 | 24.9 |
| 23.208 | 3.8294 | 683 | 39.8 |
| 23.825 | 3.7625 | 291 | 16.9 |
| 24.024 | 3.7013 | 529 | 30.8 |
| 24.959 | 3.5646 | 197 | 11.5 |
| 26.312 | 3.3842 | 152 | 8.9 |

TABLE 10-continued

| 2-Theta | d(A) | Height | Height % |
|---|---|---|---|
| 26.799 | 3.3239 | 132 | 7.7 |
| 27.240 | 3.2711 | 192 | 11.2 |
| 27.820 | 3.2042 | 130 | 7.8 |
| 28.887 | 3.0882 | 109 | 6.3 |
| 29.488 | 3.0267 | 67 | 3.9 |
| 30.072 | 2.9692 | 54 | 3.1 |
| 30.843 | 2.9151 | 196 | 11.4 |
| 31.409 | 2.8458 | 114 | 6.8 |
| 32.297 | 2.7704 | 40 | 2.9 |
| 34.501 | 2.5974 | 151 | 8.8 |
| 35.565 | 2.5221 | 50 | 3.4 |
| 35.925 | 2.4977 | 81 | 3.0 |
| 36.968 | 2.4200 | 89 | 5.2 |
| 38.144 | 2.3574 | 112 | 6.5 |
| 38.677 | 2.3261 | 47 | 2.7 |

Example 11

Characterization of Pramipexole Pamoates at a 1:1 or 2:1 Molar Ratio of Pramipexole to Pamoic Acid by Proton Nuclear Magnetic Resonance Spectroscopy ($^1$H-NMR).

Figure 21:
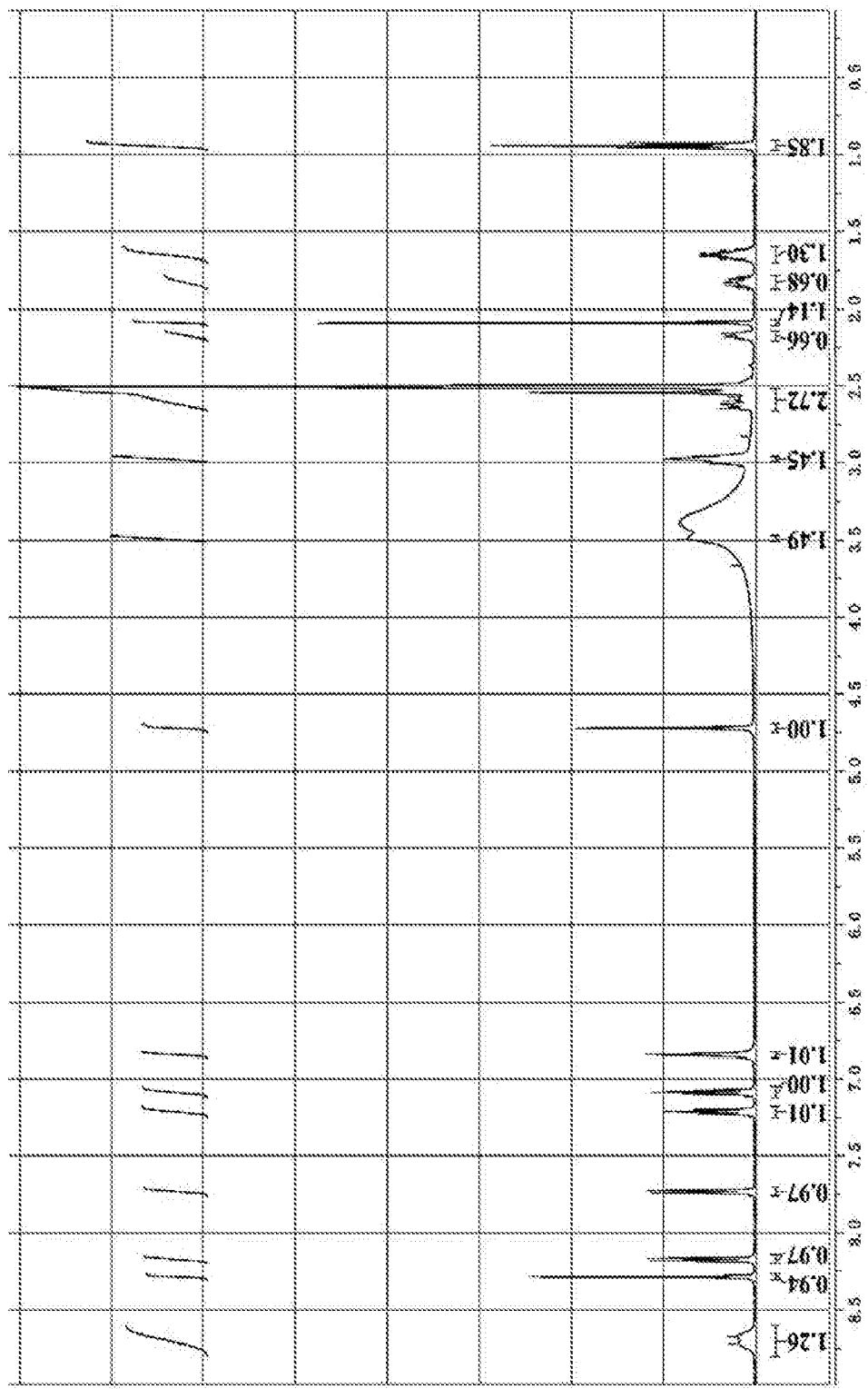
FIG. 21 depicts a $^1$H-NMR spectrum of pramipexole pamoate (1:1 molar ratio of pramipexole to pamoic acid) obtained from a mixture of acetone and water.
Figure 22:
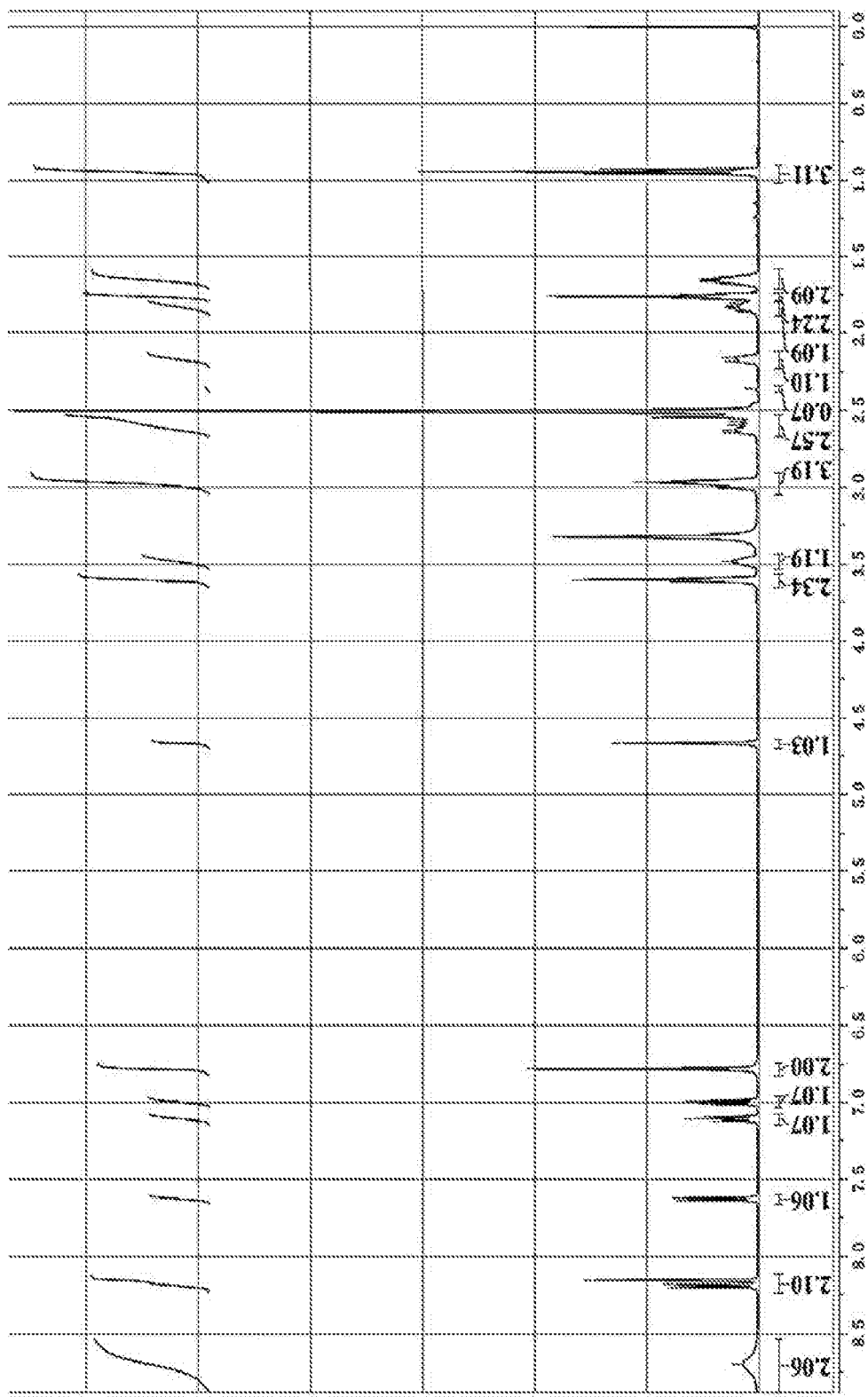
FIG. 22 depicts a $^1$H-NMR spectrum of pramipexole pamoate (2:1 molar ratio of pramipexole to pamoic acid) obtained from a solution of tetrahydrofuran.

Pramipexole pamoates (1:1 and 2:1) were analyzed using $^1$H-NMR. The $^1$H-NMR spectra are provided in FIGS. 21 and 22. FIG. 21 is the $^1$H-NMR spectrum of the 1:1 salt prepared from a mixture of acetone and water (Example 7). The molar ratio of pramiperxol to pamoic acid was approximately 1:1 measured from proton integration of the $^1$H NMR spectrum. $^1$H NMR (500 MHz, DMSO-$d_6$) chemical shifts were recorded at (all values in ppm) 8.65 (b, 2H), 8.28 (s, 2H), 8.17 (d, 2H), 7.73 (d, 2H), 7.21 (t, 2H), 7.09 (t, 2H), 6.84 (s, 2H), 4.72 (s, 2H), 3.49 (m, 3H), 2.97 (m, 3H), 2.50-2.68 (m, 6H), 2.17 (m, 1H), 1.83 (m, 1H), 1.65 (m, 2H), 0.94 (t, 3H). FIG. 22 is the $^1$H-NMR spectrum of the 2:1 salt prepared in a solution of tetrahydrofuran (Example 10). The molar ratio of pramipexole to pamoic acid was approximately 2:1 measured from proton integration of the $^1$H-NMR spectrum. $^1$H-NMR (500 MHz, DMSO-$d_6$) chemical shifts were recorded at (in ppm) 8.65 (b, 2H), 8.19 (m, 2H), 7.63 (d, 1H), 7.11 (m, 1H), 6.99 (m, 1H), 6.78 (s, 2H), 4.67 (s, 1H), 3.59 (m, 2H), 3.49 (m, 1H), 2.97 (m, 3H), 2.50-2.68 (m, 3H), 2.17 (m, 1H), 1.51-1.83 (m, 5H), 1.65 (m, 2H), 0.95 (t, 3H).

Example 12

Crystalline Form Screening of Pramipexole Pamoate Salt Using Different Solvent Systems.

This example provides a crystalline form screening summary of the pramipexole pamoate salt described in the above examples. The solvent used to prepare the crystalline form of pramipexole pamoate can be important as many solvents or solvent system did not work for the formation of crystalline salt form.

A panel of solvents or the combination of these solvents including water, alkanols (e.g. methanol and ethanol), alkyl ketones (e.g. acetone), alkanes (e.g. n-heptane), acetonitrile, toluene, DMSO, alkyl ester (e.g. ethyl acetate), halogenated alkanes (e.g. chloroform), THF, and 1,4-dioxane were screened to generate the crystalline form of the pramipexole pamoate salt. Using these solvents, different types of crystallization techniques known by one in the art were used including cooling, evaporation, and addition of a second solvent to reduce the solubility of the solute (technique known as anti-solvent or drown-out).

When a mixture of acetone and water or a mixture of acetone and methanol was used as solvent system, two different crystalline forms of a mono-pramipexole pamoate salt were obtained using amorphous pramipexole pamoate salt as depicted in Examples 7 and 8. However, as described in Examples 9 and 10, two different crystalline forms of a semi-pramipexole pamoate salt were obtained from amorphous pramipexole pamoate salt when using ethyl acetate or tetrahydrofuran (THF) as solvent system.

Between two crystalline forms of mono-pramipexole pamoate salt obtained using the above solvent systems, the form that was obtained from acetone and water in Example 7 is more stable. The form from Example 8 started converting into the crystalline form depicted in Example 7 upon standing at room temperature after 7 days. For the two crystalline forms of semi-pramipexole pamoate salt, the form described in Example 10 was more stable. The crystalline form of semi-pramipexole pamoate salt from Example 9 was converting into amorphous state when placed in the dry box at room temperature.

Example 13

Preparation of Ropinirole Pamoate at a 2:1 Molar Ratio of Ropinirole to Pamoic Acid from a Mixture of DMSO and Water.

Ropinirole (1.3 g, 5 mmol) and Pamoic Acid (0.967 g, 2.5 mmol) was added into DMSO (8 mL) with stirring to form a solution. The resultant solution was slowly added to water (250 mL) at room temperature which produced a white solid. The solid was collected on a filter, washed with water, and dried in vacuum at 45° C. to generate Ropinirole Pamoate as white solids (2.1 g, 92.6%).

Example 14

A. Preparation of Rotigotine Pamoate at a 1:1 Molar Ratio of Rotigotine to Pamoic Acid from a Mixture of DMSO and Water.

Rotigotine (3 g, 9.51 mmol) and Pamoic Acid (3.68 g, 9.51 mmol) was added into DMSO (40 mL) with stirring to form a solution. The resultant solution was slowly added to water (500 mL) at room temperature which produced a white solid. The solid was collected on a filter, washed with water, and dried in vacuum at 45° C. to generate Rotigotine Pamoate as white solids (5 g, 74.9%).

B. Preparation of Rotigotine Pamoate at a 2:1 Molar Ratio of Rotigotine to Pamoic Acid from a Mixture of DMSO and Water.

Rotigotine (1 g, 3.17 mmol) and Pamoic Acid (0.614 g, 1.585 mmol) was added into DMSO (8 mL) with stirring to form a solution. The resultant solution was slowly added to water (500 mL) at room temperature which produced a white solid. The solid was collected on a filter, washed with water, and dried in vacuum at 45° C. to generate Rotigotine Pamoate as white solids (2 g, 77.4%).

Example 15

Preparation of Pramipexole Pamoate at a 1:1 Molar Ratio of Pramipexole to Pamoic Acid from a Mixture of DMSO and Ethyl Acetate (EA).

Pramipexole (5.0 g, 23.44 mmol) and Pamoic acid (9.08 g, 23.44 mmol) was dissolved by stirring at room temperature in DMSO (50 mL). The solution was then slowly added to ethyl acetate (2 L) at room temperature to generate a white solid. The solid was collected on a filter and dried in vacuum at 45° C. to give pramipexole pamoate at a 1:1 Molar ratio of Pramipexole to Pamoic acid (14.0 g, 99.0%).

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. A crystalline Form I of pamoate salt of rotigotine, which is characterized by an X-ray Powder diffraction ("XRPD") spectrum having both peaks at 4.6 and 9.3, ±0.2° 2-theta.

2. A crystalline form of pamoate salt of ropinirole, wherein the crystalline form is Form A, Form B, Form C, Form D, or Form E, wherein Form A is characterized by an XRPD spectrum having the following peaks: 4.3, 17.1, 18.6, and 20.5, ±0.2° 2-theta;

Form B is characterized by an XRPD spectrum having the following peaks: 11.5, 16.4, 21.0, 23.1, 23.4, and 26.2, ±0.2° 2-theta;

Form C is characterized by an XRPD spectrum having peaks at 16.1 and 18.8, ±0.2° 2-theta;

Form D is characterized by an XRPD spectrum having the following peaks: 14.3, 17.9, and 25.2, ±0.2° 2-theta; and Form E is characterized by an XRPD spectrum having the following peaks: 11.7, 12.0, and 21.0, ±0.2° 2-theta.

3. The crystalline form of claim 2, which is Form A, wherein the Form A is characterized by an XRPD spectrum having the following peaks: 4.3, 9.8, 17.1, 18.6, 19.1, 20.5, 21.0, and 23.1, ±0.2° 2-theta.

4. The crystalline form of claim 2, which is Form B, wherein the Form B is characterized by an XRPD spectrum having the following peaks: 11.5, 12.0, 12.7, 16.4, 21.0, 23.1, 23.4, and 26.2, ±0.2° 2-theta.

5. The crystalline form of claim 2, which is Form C, wherein the Form C is characterized by an XRPD spectrum having the following peaks: 8.0, 9.5, 16.1, and 18.8, ±0.2° 2-theta.

6. The crystalline form of claim 2, which is Form D, wherein the Form D is characterized by (a) an XRPD spectrum having the following peaks: 14.3, 17.9, 21.5, 22.4, 24.8, and 25.2, ±0.2° 2-theta.

7. The crystalline form of claim 2, which is Form E, wherein the Form E is characterized by an XRPD spectrum having the following peaks: 11.1, 11.7, 12.0, 21.0, 26.1, and 26.6, ±0.2° 2-theta.

8. A crystalline form of of pramipexole, wherein the crystalline form is Form 1, Form 2, Form 3, or Form 4, wherein Form 1 is characterized by an XRPD spectrum having one or more of the following peaks: 13.8, 15.3, and 21.1, ±0.2° 2-theta;

Form 2 is characterized by an XRPD spectrum having one or more of the following peaks: 12.0, 15.0, 20.4, and 20.9, ±0.2° 2-theta;

Form 3 is characterized by an XRPD spectrum having one or more of the following peaks: 10.7, 12.7, 13.5, and 14.9, ±0.2° 2-theta; and Form 4 is characterized by an XRPD spectrum having the following peaks: 6.1, and 17.9, ±0.2° 2-theta.

9. The crystalline form of claim 8, which is Form 1, wherein the Form 1 is characterized by an XRPD spectrum having the following peaks: 7.7, 11.8, 13.8, 15.3, 18.9, 21.1, 23.1, 23.7, and 26.4, ±0.2° 2-theta.

10. The crystalline form of claim 8, which is Form 2, wherein the Form 2 is characterized by an XRPD spectrum having the following peaks: 12.0, 15.0, 20.4, 20.9, 22.5, and 23.3, ±0.2° 2-theta.

11. The crystalline form of claim 8, which is Form 3, wherein the Form 3 is characterized by an XRPD spectrum having the following peaks: 10.7, 12.7, 13.5, 14.9, 18.7, and 22.3, ±0.2° 2-theta.

12. The crystalline form of claim 8, which is Form 4, wherein the Form 4 is characterized by (a) an XRPD spectrum having the following peaks: 6.1, 17.9, 21.3, and 23.2, ±0.2° 2-theta.

13. A pharmaceutical composition comprising the crystalline form of claim 8 and a pharmaceutically acceptable carrier.

14. The pharmaceutical composition of claim 13, wherein the pharmaceutically acceptable carrier is a viscous aqueous or nonaqueous carrier.

15. The crystalline form of claim 8, which is Form 1, wherein the Form 1 is characterized by an XRPD spectrum substantially in accordance with that shown in FIG. 13.

16. The crystalline form of claim 8, which is Form 2, wherein the Form 2 is characterized by an XRPD spectrum having the following peaks: 12.0, 15.0, 17.2, 20.4, 20.9, 22.5, 23.3, and 25.4, ±0.2° 2-theta.

17. The crystalline form of claim 8, which is Form 2, wherein the Form 2 is characterized by an XRPD spectrum substantially in accordance with that shown in FIG. 15.

18. The crystalline form of claim 8, which is Form 3, wherein the Form 3 is characterized by an XRPD spectrum having the following peaks: 10.7, 12.7, 13.5, 14.9, 16.3, 18.1, 18.7, and 22.3, ±0.2° 2-theta.

19. The crystalline form of claim 8, which is Form 3, wherein the Form 3 is characterized by an XRPD spectrum substantially in accordance with that shown in FIG. 17.

20. The crystalline form of claim 8, which is Form 4, wherein the Form 4 is characterized by an XRPD spectrum having the following peaks: 6.1, 17.9, 18.9, 21.3, 23.2, and 24.0, ±0.2° 2-theta.

21. The crystalline form of claim 8, which is Form 4, wherein the Form 4 is characterized by an XRPD spectrum having the following peaks: 6.1, 13.5, 14.9, 17.9, 18.9, 21.3, 21.8, 22.4, 23.2, and 24.0, ±0.2° 2-theta.

22. The crystalline form of claim 8, which is Form 4, wherein the Form 4 is characterized by an XRPD spectrum substantially in accordance with that shown in FIG. 19.

23. The crystalline form of claim 2, which is Form A, wherein the Form A is characterized by an XRPD spectrum substantially in accordance with that shown in FIG. 1.

24. The crystalline form of claim 2, which is Form B, wherein the Form B is characterized by an XRPD spectrum substantially in accordance with that shown in FIG. 3.

25. The crystalline form of claim 2, which is Form C, wherein the Form C is characterized by an XRPD spectrum substantially in accordance with that shown in FIG. 5.

26. The crystalline form of claim 2, which is Form D, wherein the Form D is characterized by an XRPD spectrum substantially in accordance with that shown in FIG. 7.

27. The crystalline form of claim 2, which is Form E, wherein the Form E is characterized by an XRPD spectrum substantially in accordance with that shown in FIG. 9.

28. The crystalline form I of claim 1, characterized by an XRPD spectrum substantially in accordance with that shown in FIG. 11.

* * * * *